United States Patent
Edwards et al.

(10) Patent No.: US 8,627,821 B2
(45) Date of Patent: Jan. 14, 2014

(54) METHOD AND DEVICE FOR DECREASING CONTAMINATION

(75) Inventors: David A. Edwards, Boston, MA (US); Mark J. Gabrielson, Ridgefield, CT (US); Robert William Clarke, Canton, MA (US); Wesley H. Dehaan, Chelmsford, MA (US); Matthew Frederick Brande, Bristol, CT (US); Jonathan Chun-Wah Man, Bellevue, WA (US)

(73) Assignee: Pulmatrix, Inc., Lexington, MA (US)

( * ) Notice: Subject to any disclaimer, the term of this patent is extended or adjusted under 35 U.S.C. 154(b) by 1724 days.

(21) Appl. No.: 11/827,031

(22) Filed: Jul. 10, 2007

(65) Prior Publication Data

US 2008/0038207 A1 Feb. 14, 2008

Related U.S. Application Data

(63) Continuation-in-part of application No. PCT/US2006/000618, filed on Jan. 10, 2006, which is a continuation-in-part of application No. PCT/US2007/008815, filed on Apr. 11, 2007.

(60) Provisional application No. 60/642,643, filed on Jan. 10, 2005, provisional application No. 60/682,356, filed on May 18, 2005, provisional application No. 60/744,729, filed on Apr. 12, 2006.

(51) Int. Cl.
| | |
|---|---|
| *A62B 7/00* | (2006.01) |
| *A61M 15/00* | (2006.01) |
| *A61M 16/00* | (2006.01) |
| *F16K 31/02* | (2006.01) |
| *A62B 9/00* | (2006.01) |
| *A61B 5/08* | (2006.01) |

(52) U.S. Cl.
USPC ............ 128/205.22; 128/205.27; 128/200.24; 128/202.22; 128/204.21; 128/204.22; 128/204.23; 128/205.23; 600/529; 600/530; 600/531; 600/532; 600/533; 600/534; 600/535; 600/536; 600/537; 600/538; 600/539; 600/540; 600/541; 600/542; 600/543

(58) Field of Classification Search
USPC ............ 128/205.27, 200.24, 202.22, 204.21, 128/204.22, 204.23, 205.23; 435/6, 7.1, 435/287.2; 436/71, 73, 86; 600/529–543
See application file for complete search history.

(56) References Cited

U.S. PATENT DOCUMENTS

| | | | |
|---|---|---|---|
| 4,370,986 A | | 2/1983 | Gebhart |
| 5,038,792 A | * | 8/1991 | Mault ........................... 600/531 |

(Continued)

FOREIGN PATENT DOCUMENTS

| | | |
|---|---|---|
| CN | 1286630 A | 3/2001 |
| DE | 2938856 | 4/1981 |

(Continued)

OTHER PUBLICATIONS

Lipp et al., "Solving Medical Problems with Chemical Engineering," Chemtech, 42-57 (1997).

(Continued)

*Primary Examiner* — Patricia Bianco
*Assistant Examiner* — Nihir Patel
(74) *Attorney, Agent, or Firm* — McDermott Will & Emery LLP

(57) ABSTRACT

Methods and devices to determine rate of particle production and the size range for the particles produced for an individual are described herein. The device (10) contains a mouthpiece (12), a filter (14), a low resistance one-way valve (16), a particle counter (20) and a computer (30). Optionally, the device also contains a gas flow meter (22). The data obtained using the device can be used to determine if a formulation for reducing particle exhalation should be administered to an individual.

25 Claims, 15 Drawing Sheets

(56) References Cited

U.S. PATENT DOCUMENTS

| | | |
|---|---|---|
| 5,042,501 A | 8/1991 | Kenny et al. |
| 5,230,884 A | 7/1993 | Evans et al. |
| 5,709,202 A | 1/1998 | Lloyd et al. |
| 5,855,913 A | 1/1999 | Hanes et al. |
| 5,883,084 A | 3/1999 | Peterson et al. |
| 5,985,309 A | 11/1999 | Edwards et al. |
| 6,083,922 A | 7/2000 | Montgomery |
| RE37,053 E | 2/2001 | Edwards et al. |
| 6,435,019 B1 * | 8/2002 | Vojtisek-Lom ............ 73/114.69 |
| 6,435,183 B1 * | 8/2002 | Farman .................... 128/204.25 |
| 6,491,872 B1 | 12/2002 | Wick |
| 7,392,806 B2 * | 7/2008 | Yuen et al. ............... 128/205.27 |
| 2001/0008632 A1 | 7/2001 | Freund et al. |
| 2004/0009128 A1 | 1/2004 | Rabinowitz et al. |
| 2004/0077093 A1 | 4/2004 | Pan |
| 2008/0257358 A1 * | 10/2008 | Stern et al. ............... 128/207.16 |

FOREIGN PATENT DOCUMENTS

| | | |
|---|---|---|
| WO | WO97/36574 | 10/1997 |
| WO | WO97/44013 | 11/1997 |
| WO | WO99/04859 | 2/1999 |
| WO | WO02/09574 | 2/2002 |
| WO | WO2004/058064 | 7/2004 |
| WO | WO2006/076265 | 7/2006 |

OTHER PUBLICATIONS

Edward et al., "Inhaling to Mitigate Exhaled Bioaerosols," Proceedings of the National Academy of Sciences of the United States of America, 101:17383-17388 (2004).

International Search Report, Written Opinion and The International Preliminary Report on Patentability in corresponding PCT Application No. PCT/US2006/000618.

International Search Report, Written Opinion and The International Preliminary Report on Patentability in corresponding PCT Application No. PCT/US2007/00815.

* cited by examiner

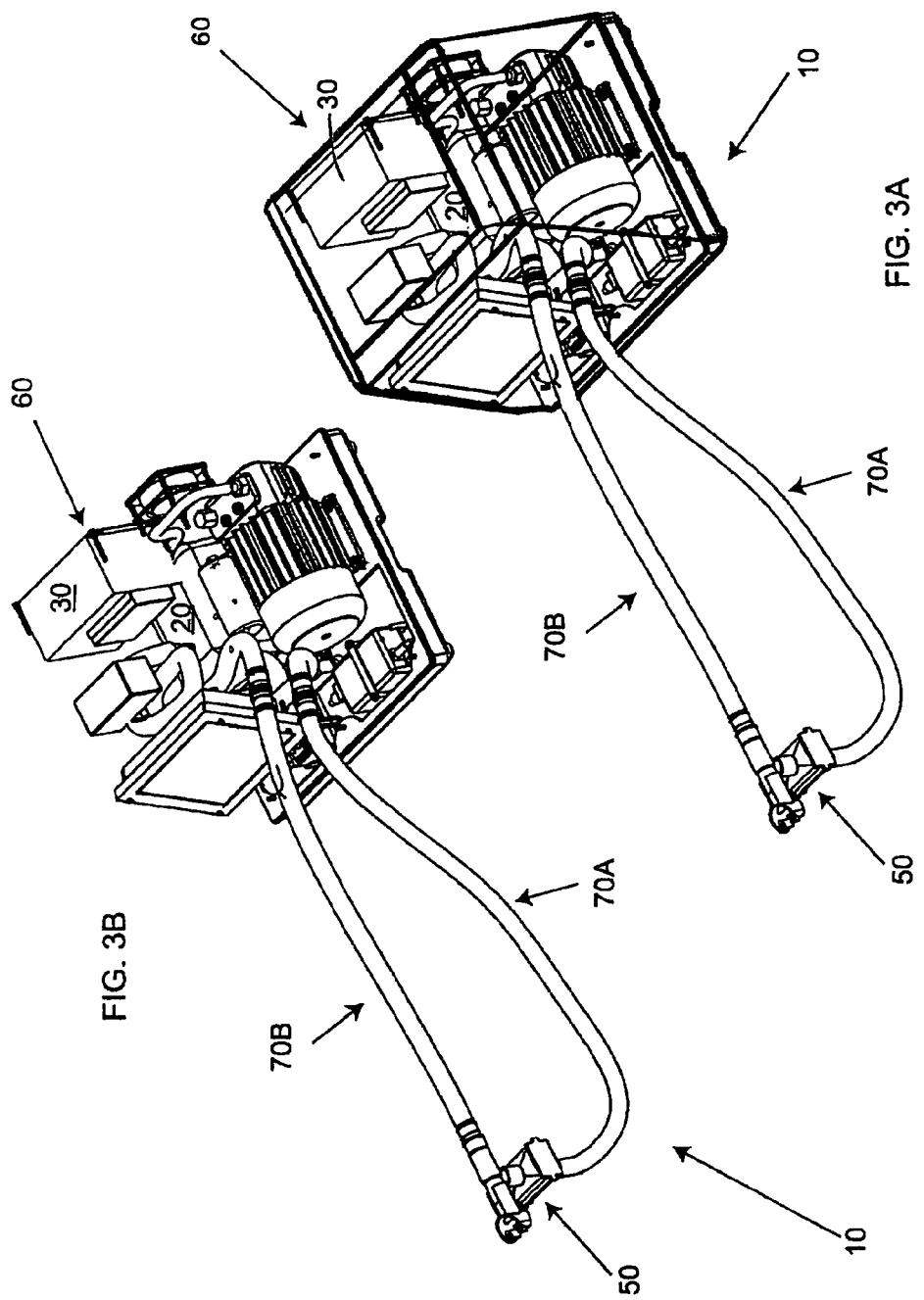

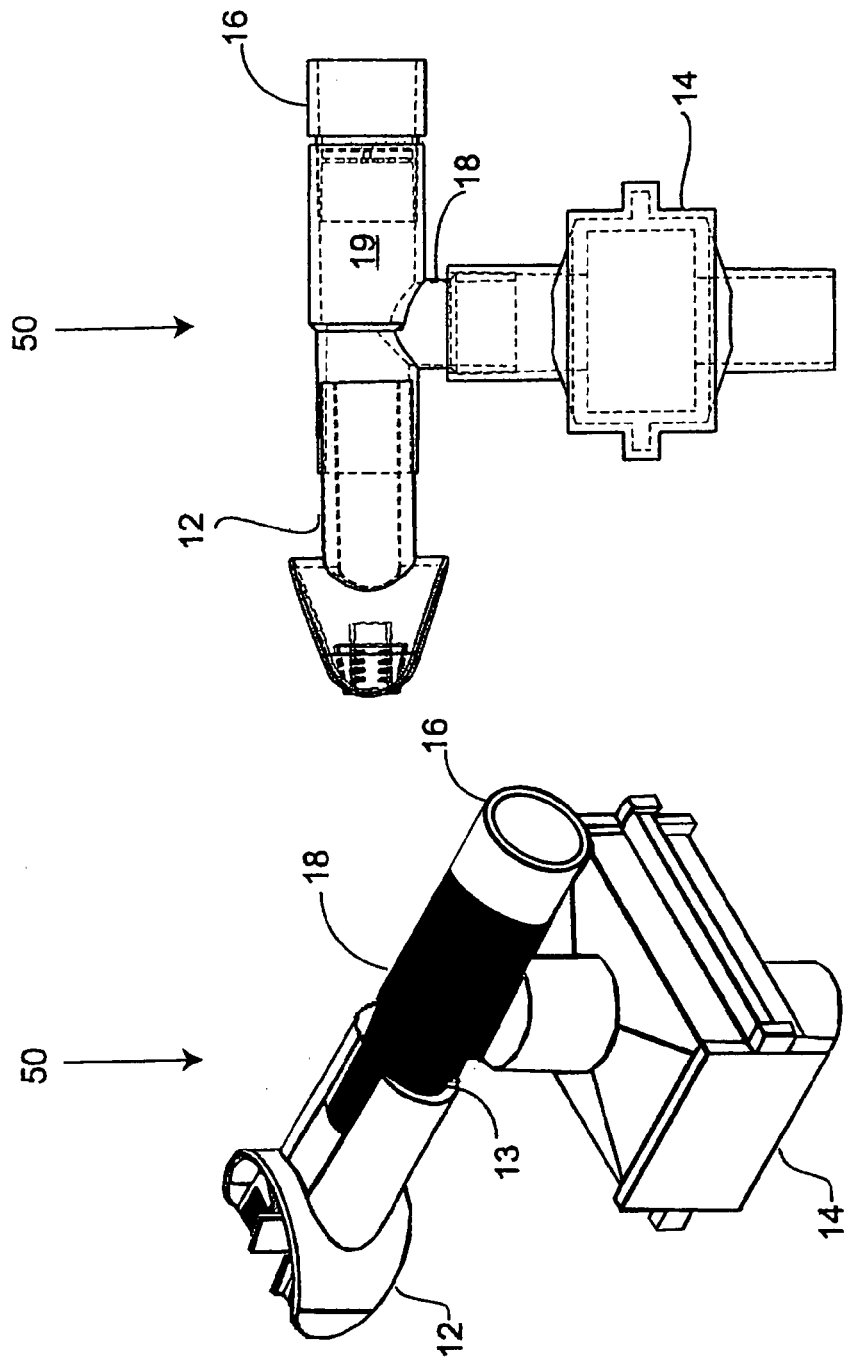

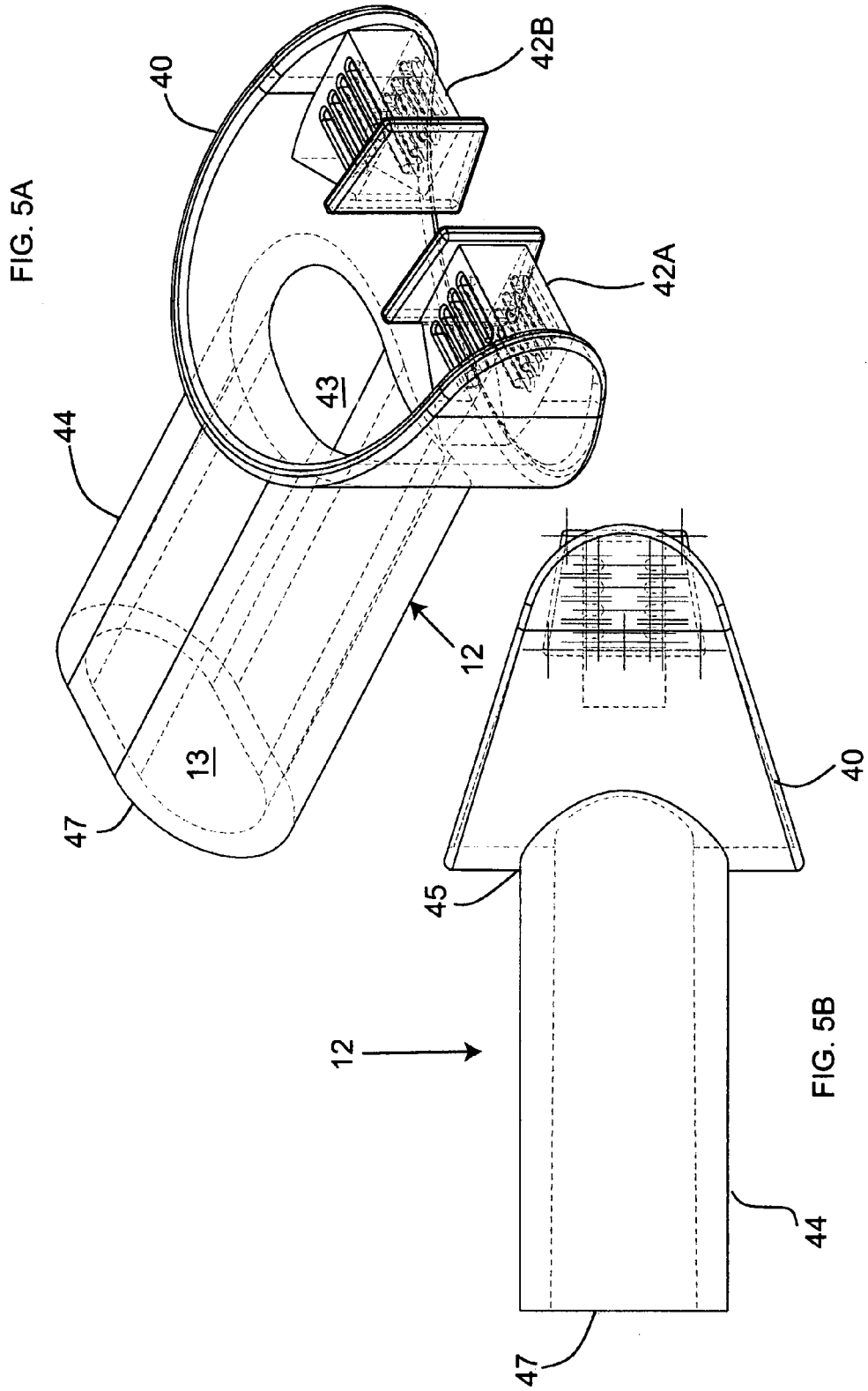

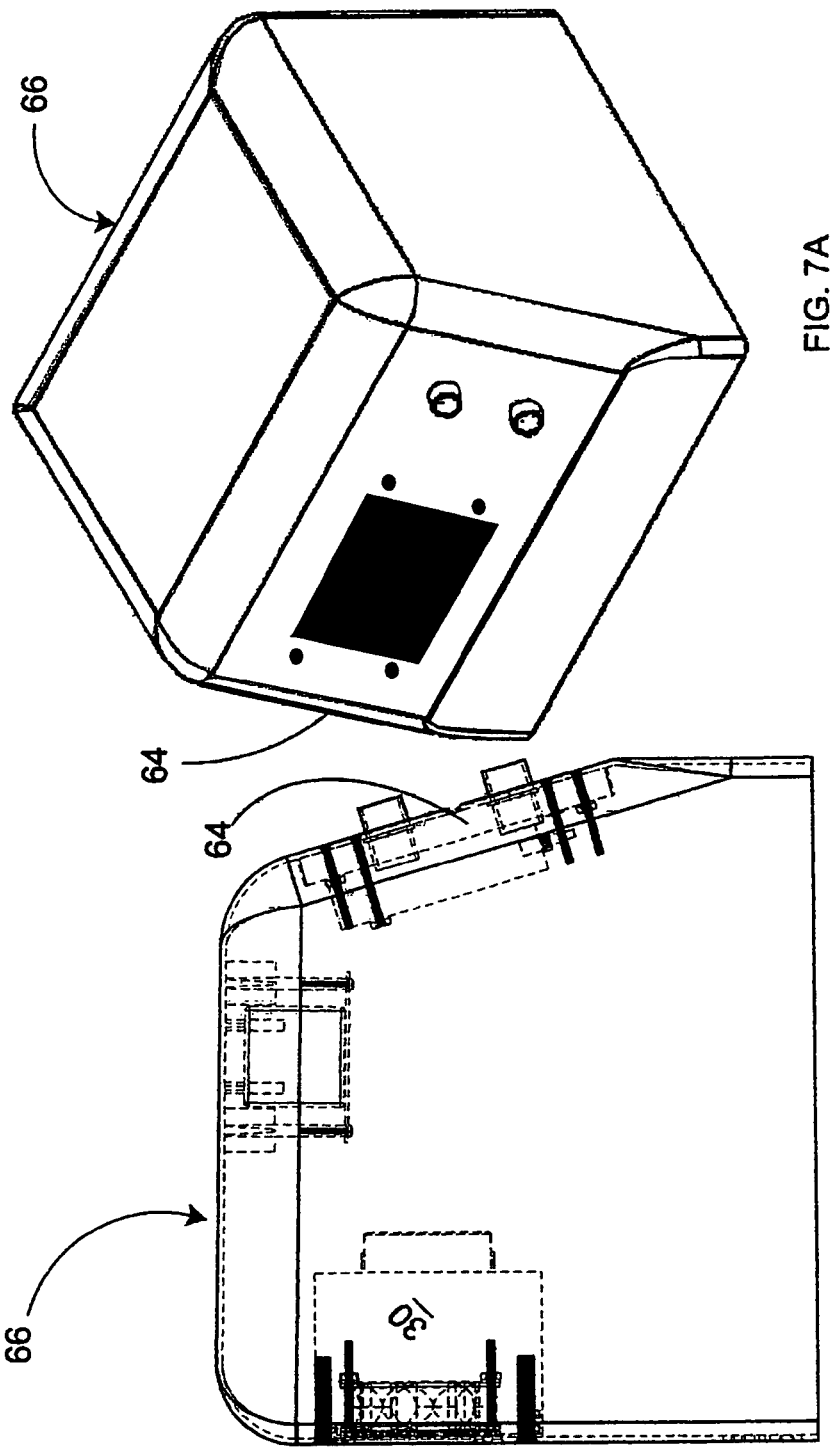

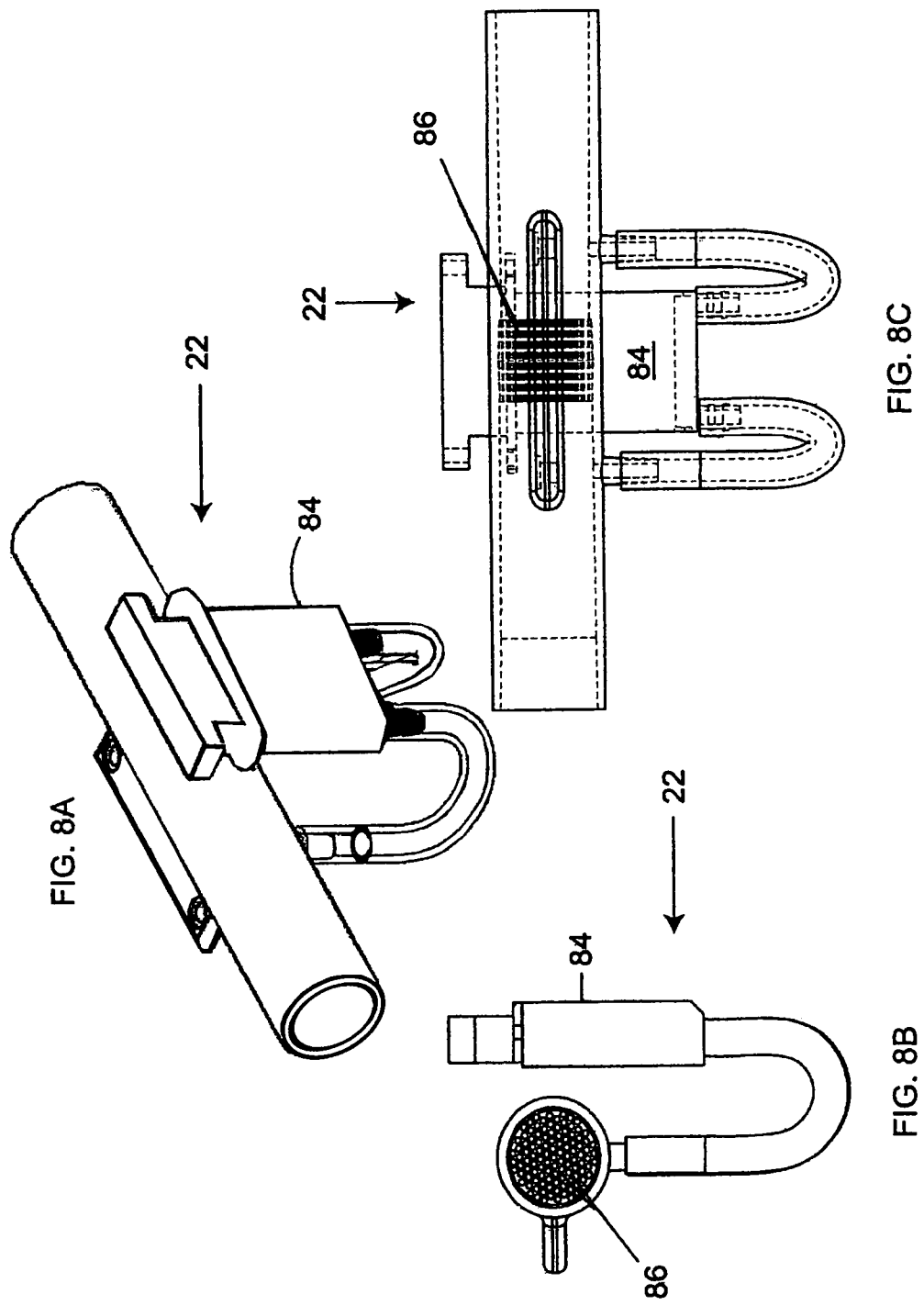

FIG. 9A
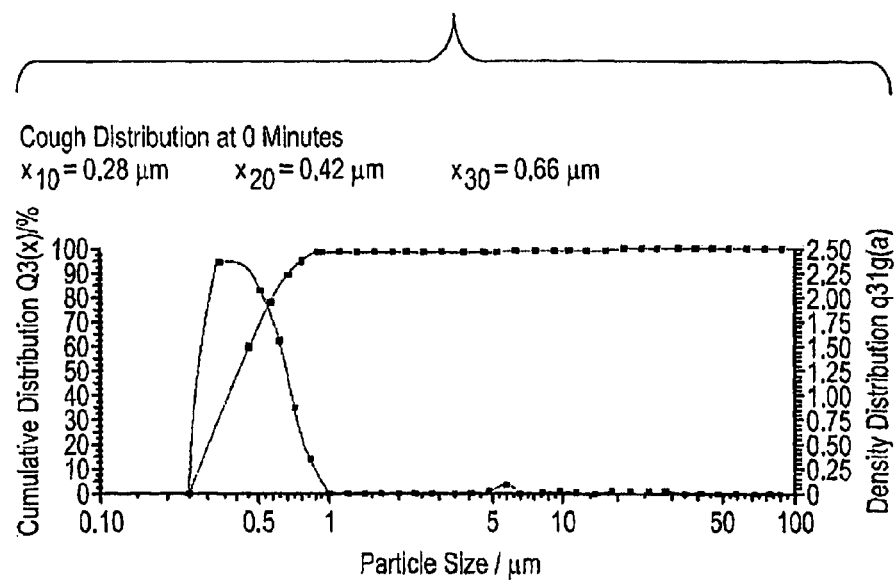
Cough Distribution at 0 Minutes
$x_{10} = 0.28$ µm     $x_{20} = 0.42$ µm     $x_{30} = 0.66$ µm
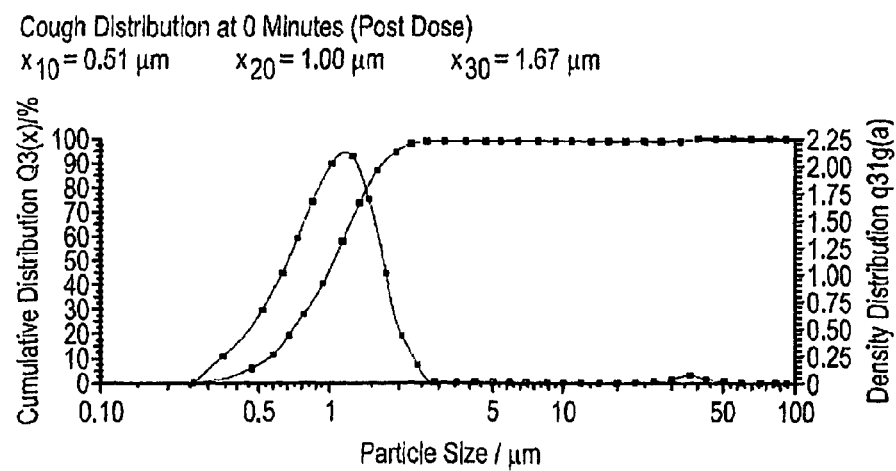
Cough Distribution at 0 Minutes (Post Dose)
$x_{10} = 0.51$ µm     $x_{20} = 1.00$ µm     $x_{30} = 1.67$ µm FIG. 9B
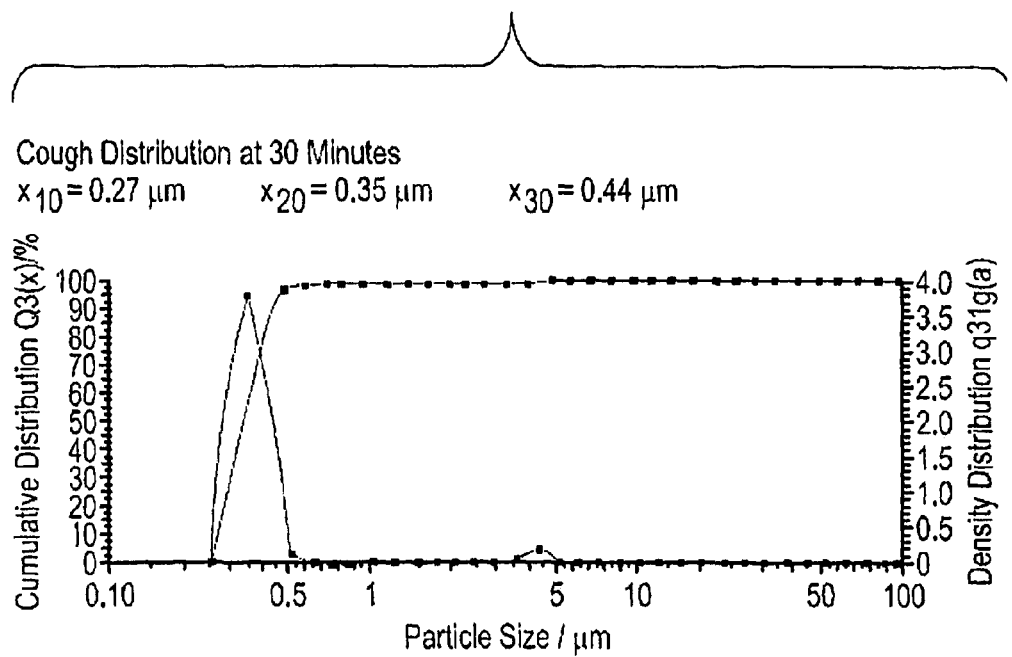
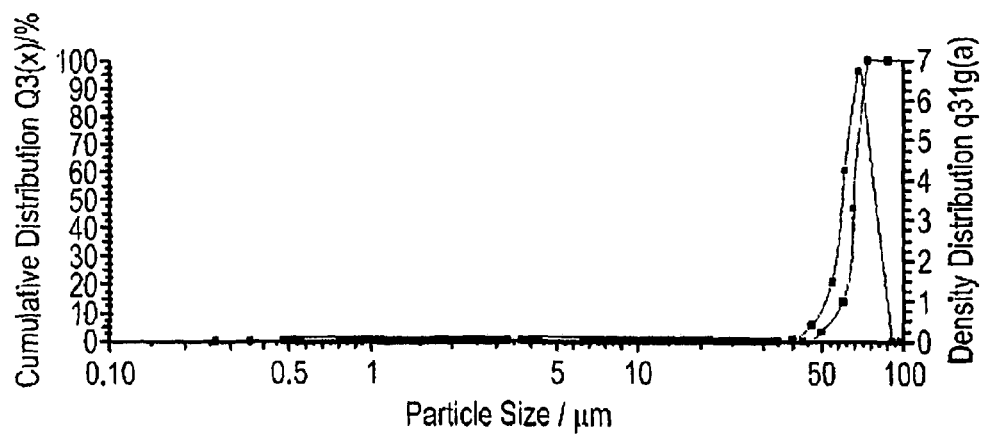

FIG. 9C
Cough Distribution at 60 Minutes
$x_{10} = 0.27$ μm    $x_{20} = 0.35$ μm    $x_{30} = 0.44$ μm
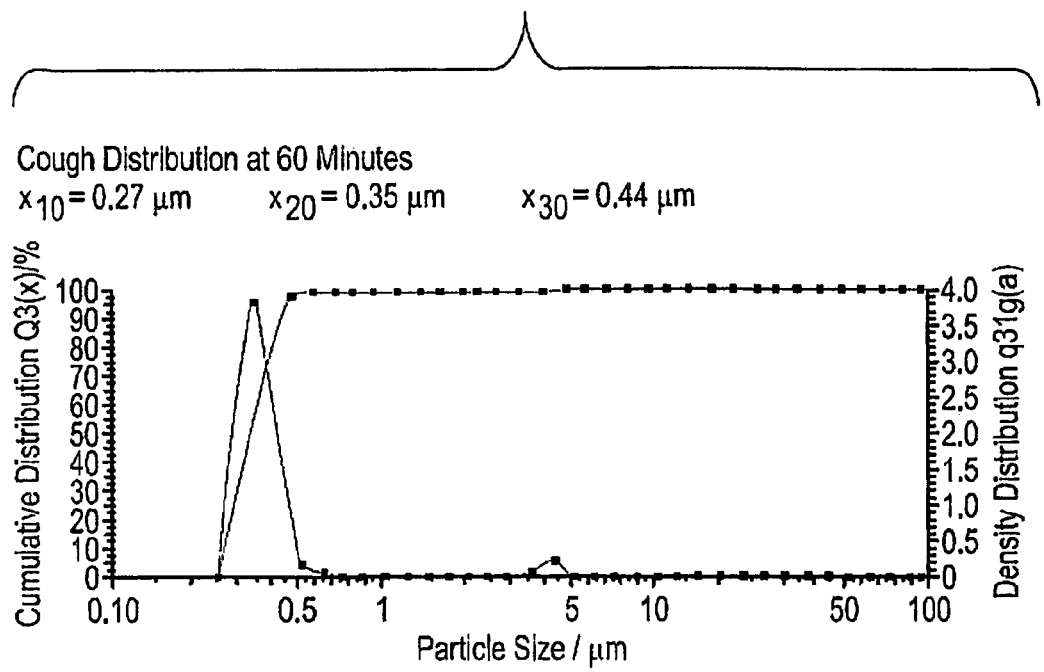
Cough Distribution at 60 Minutes (Post Dose)
$x_{10} = 25.58$ μm    $x_{20} = 31.71$ μm    $x_{30} = 36.90$ μm
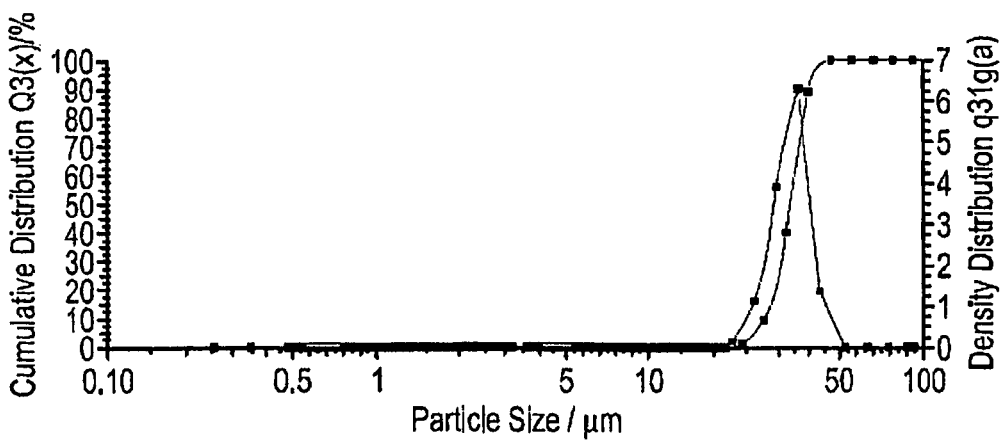

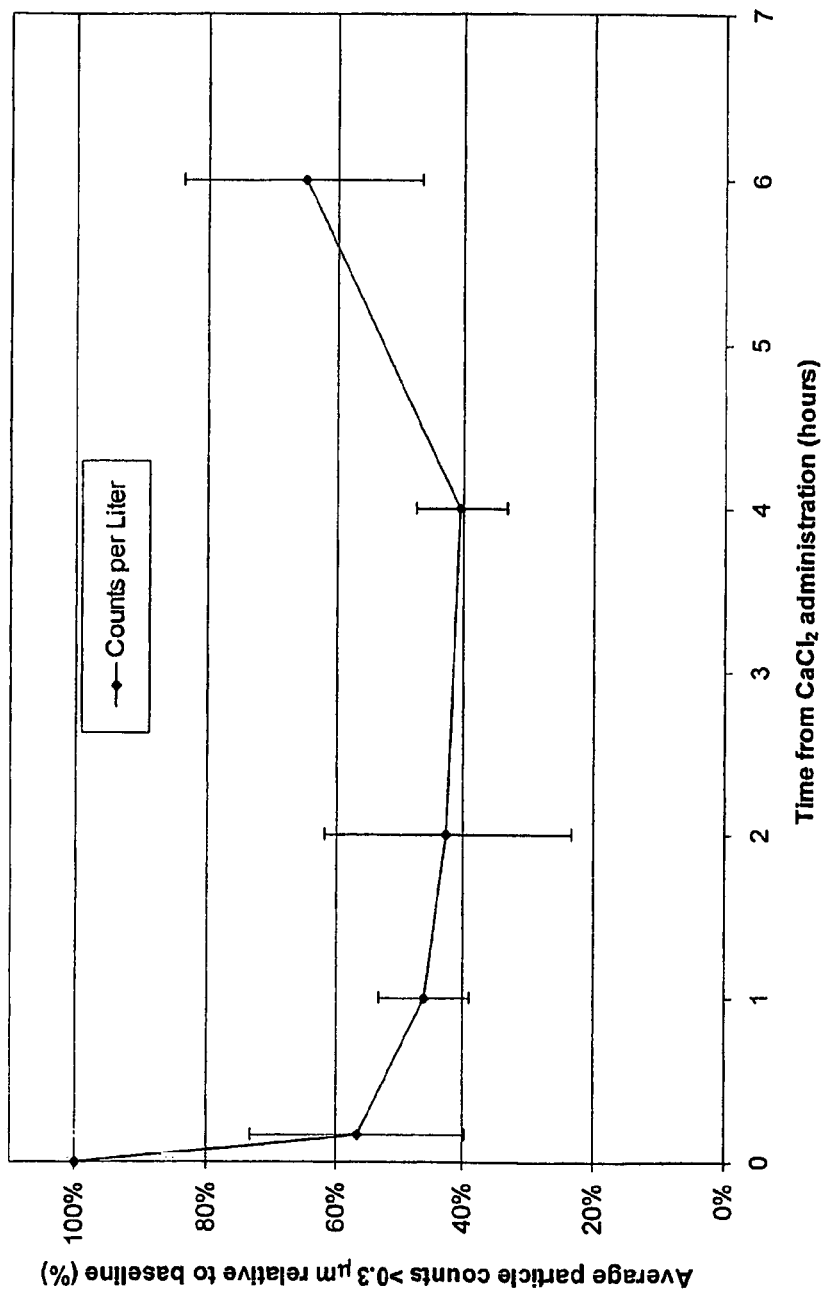

METHOD AND DEVICE FOR DECREASING CONTAMINATION

CROSS-REFERENCE TO RELATED APPLICATIONS

This application is a continuation-in-part of International Application PCT/US2006/000618, filed Jan. 10, 2006, which claims priority to U.S. Ser. No. 60/642,643, filed Jan. 10, 2005, International Application PCT/US2005/006903 filed Mar. 3, 2005, and U.S. Ser. No. 60/682,356, filed May 18, 2005. This application is also a continuation-in-part of International Application PCT/US2007/008815, filed Apr. 11, 2007, which claims priority to U.S. Ser. No. 60/744,729, filed Apr. 12, 2006.

FIELD OF THE INVENTION

The present invention is in the field of methods, formulations and devices to measure and decrease particle exhalation and contamination in various environments, and is particularly useful in cleanrooms.

BACKGROUND OF THE INVENTION

A cleanroom is a controlled environment where products are manufactured. It is a room in which the concentration of airborne particles is controlled to specified limits. Eliminating sub-micron airborne contamination is really a process of control. These contaminants are generated by people, process, facilities and equipment. They must be continually removed from the air. The level to which these particles need to be removed depends upon the standards required. The most frequently used standard is the Federal Standard 209E. The 209E is a document that establishes standard classes of air cleanliness for airborne particulate levels in cleanrooms and clean zones. Strict rules and procedures are followed to prevent contamination of the product.

The following table shows the latest cleanroom classifications. Note that ISO Class 2 is equivalent to 209 Class 10.

It only takes a quick monitor of the air in a cleanroom compared to a typical office building to see the difference. Typical office building air contains from 500,000 to 1,000,000 particles (0.5 microns or larger) per cubic foot of air. A Class 100 cleanroom is designed to never allow more than 100 particles (0.5 microns or larger) per cubic foot of air. Class 1000 and Class 10,000 cleanrooms are designed to limit particles to 1000 and 10,000 respectively.

A human hair is about 75-100 microns in diameter. A particle 200 times smaller (0.5 micron) than the human hair can cause major disaster in a cleanroom. Contamination can lead to expensive downtime and increased production costs. Once a cleanroom is built, it must be maintained and cleaned to the same high standards.

Contamination is a process or act that causes materials or surfaces to be soiled with contaminating substances. There are two broad categories of surface contaminants: film type and particulates. These contaminants can produce a "killer defect" in a miniature circuit. Film contaminants of only 10 nm (nanometers) can drastically reduce coating adhesion on a wafer or chip. It is widely accepted that particles of 0.5 microns or larger are the target. However, some industries are now targeting smaller particles.

A partial list of contaminants is provided below. Any of these can be the source for killing a circuit. Preventing these contaminants from entering the cleanroom environment is a major objective. It has been found that many of these contaminants are generated from five basic sources: facilities, people, tools, fluids and the product being manufactured.

1. Facilities: Walls, floors and ceilings; Paint and coatings; Construction material (sheet rock, saw dust etc.); Air conditioning debris; Room air and vapors; Spills and leaks
2. People: Skin flakes and oil; Cosmetics and perfume; Spittle; Clothing debris (lint, fibers etc.); Hair
3. Tool Generated: Friction and wear particles; Lubricants and emissions; Vibrations; Brooms, mops and dusters
4. Fluids: Particulates floating in air; Bacteria, organics and moisture; Floor finishes or coatings; Cleaning chemicals; Plasticizers (outgasses); Deionized water

TABLE 1

| Classification numbers | Airborne Particulate Cleanliness Classes |||||
|---|---|---|---|---|---|
| | Maximum concentration limits (particles/m$^3$ of air) for particles equal to and larger than the sizes listed below |||||
| numbers (N) | 0.1 micron | 0.2 micron | 0.3 micron | 0.5 micron | 1 micron | 5 micron |
| ISO 1 | 10 | 2 | | | | |
| ISO 2 | 100 | 24 | 10 | 4 | | |
| ISO 3 | 1,000 | 237 | 102 | 35 | 8 | |
| ISO 4 | 10$^4$ | 2,370 | 1,020 | 352 | 83 | |
| ISO 5 | 10$^5$ | 23,700 | 10,200 | 3,520 | 832 | 29 |
| ISO 6 | 10$^6$ | 237,000 | 102,000 | 35,200 | 8,320 | 293 |
| ISO 7 | | | | 352,000 | 83,200 | 2,930 |
| ISO 8 | | | | 3,520,000 | 832,000 | 29,300 |
| ISO 9 | | | | 35,200,000 | 8,320,000 | 293,000 |

The only way to control contamination is to control the total environment. Air flow rates and direction, pressurization, temperature, humidity and specialized filtration all need to be tightly controlled. The sources of these particles also need to controlled or eliminated whenever possible. Cleanrooms are planned and manufactured using strict protocol and methods. They are frequently found in electronics, pharmaceutical, biopharmaceutical, medical device industries and other critical manufacturing environments.

5. Product generated: Silicon chips; Quartz flakes; Cleanroom debris; Aluminum Particles Current methods and devices used to decrease contamination include HEPA (High Efficiency Particulate Air) filters. These filters are extremely important for maintaining contamination control. They filter particles as small as 0.3 microns with a 99.97% minimum particle-collective efficiency. Cleanrooms are designed to achieve and maintain an airflow in which essentially the entire body of air within a confined area moves with uniform velocity along parallel flow lines. This air flow is called laminar flow. The more restriction of air flow the more turbulence. Turbulence can cause particle movement. In addition to the HEPA filters commonly used in cleanrooms, there are a number of other filtration mechanisms used to remove particles from gases and liquids. These filters are essential for providing effective contamination control. Cleaning is also an essential element of contamination control. The requirements for cleanroom garments will vary from location to location. Gloves, face masks and head covers are standard in nearly every cleanroom environment. Smocks are being used more and more. Jump suits are required in very clean environments. Care must be taken when selecting and using commodity items in cleanrooms. Wipers, cleanroom paper and pencils and other supplies that service the cleanroom should be carefully screened and selected. Review of the local cleanroom requirements for approving and taking these items into the cleanroom is essential. In fact, many cleanroom managers will have approval lists of these types of items.

There are both physical and psychological concerns when humans are present in cleanrooms. Physical behavior like fast motion and horseplay can increase contamination. Psychological concerns like room temperature, humidity, claustrophobia, odors and workplace attitude are important. Ways people produce contamination include body regenerative processes resulting in skin flakes, oils, perspiration and hair; behavior including the rate of movement, sneezing and coughing; attitude in the work habits and communication between workers. People are a major source of contamination in the cleanroom, as demonstrated below in table 2. Table 2 lists a person's typical activities and the corresponding rate or particle production (number of particles produced per minute). The particles are 0.3 microns and larger.

TABLE 2

Typical activities and rate of particle production

| People Activity | Rate of Particle (0.3 microns and larger) Production (particles/minute) |
|---|---|
| Motionless (Standing or Seated) | 100,000 |
| Walking about 2 mph | 5,000,000 |
| Walking about 3.5 mph | 7,000,000 |
| Walking about 5 mph | 10,000,000 |
| Horseplay | 100,000,000 |

It is an object of the present invention to provide a device and methods for use in decreasing contamination in environments such as cleanrooms.

It is further an object of the present invention to provide a method for decreasing or limiting the airborne transmission of viruses and bacteria in environments such as cleanrooms.

It is yet a further object of this invention to manufacture a device for the measurement of exhaled particle number and particle size to determine if a formulation for decreasing particle exhalation is needed.

It is an object of the present invention to provide a method for using a device for the measurement of exhaled particles by individuals.

SUMMARY OF THE INVENTION

Methods and devices to determine rate of particle production and the size range for the particles produced for an individual are described herein. The device (10) contains a mouthpiece (12), a filter (14), a low resistance one-way valve (16), a particle counter (20) and a computer (30). Optionally, the device also contains a gas flow meter (22). The data obtained using the device can be used to determine if a formulation for reducing particle exhalation is needed. This device is particularly useful prior to and/or following entry in a cleanroom to ensure that the cleanroom standards are maintained. The device can also be used to identify animals and humans who have an enhanced propensity to exhale aerosols (referred to herein as "over producers", "super-producers", or "superspreaders").

The invention provides a diagnostic device comprising a disposable kit (50) and a main housing (60). The disposable kit (50) can be functionally connected to the main housing (60) to provide for airflow between an individual and the main housing (60). In certain embodiments, the disposable kit (50) is connected to the main housing (60) with one or more connecting tubes (70A and 70B) exterior to the main housing (60). The disposable kit (50) comprises a mouthpiece (12), a filter (14), a connector (18), and a one-way valve (16). The components of the disposable kit (50) are optionally formed from biodegradable materials. The mouthpiece (12) of the disposable kit allows for creation of a sealed passage between the airway of an individual and the diagnostic device. The mouthpiece (12) can be made of a flexible material (e.g., rubber and/or plastic) for purpose of creating a firm seal. The filter (14) of the disposable kit (50) is typically a high-efficiency, low pressure drop filter, optionally with a bacterial/viral removal efficiency of greater than 99.99%. The main housing (60) of the diagnostic device comprises a particle counter (20), and optionally comprises a computer (30), gas flow meter (22), display (64), and/or vacuum pump (62).

The invention provides a diagnostic device for measuring particle exhalation in an individual, comprising a disposable kit and a main housing, the disposable kit comprising a mouthpiece, a two-way filter, and a low resistance one-way valve; the main housing comprising a particle counter and a computer, and wherein the mouthpiece has an outlet connected to the filter and to the one-way valve, the filter exposed to the ambient environment at one end and connected to the mouthpiece at the other end, and the disposable kit connected to the main housing via two connecting tubes.

Preferably, the filter is capable of removing particles having a size greater than or equal to 0.1 microns in diameter. In another embodiment, the mouthpiece is a mouthpiece designed for a user to place his lips around, nasal prongs, a mask that is capable of covering a user's mouth and nose, or a mask that is capable of covering a user's nose. The mouthpiece may comprise a curved flange and two protrusions, wherein the mouthpiece is designed for a user to place the flange between his lips and teeth to form a seal when the user bites down on the protrusions.

The filter may be a combination of two or more filters, the particle counter may be an electrical mobility particle counter, an impaction particle counter, an electrostatic impaction particle counter, an infrared spectroscopy particle counter, a laser diffraction particle counter, a light scattering particle counter, or an optical particle counter. The particle counter is preferrably connected to the computer in a manner that allows control commands to be sent from the computer to the particle counter.

The computer can be a microprocessor internal or external to the particle counter. The device further may comprise a gas flow meter connected to the filter and located between the filter and the ambient environment, preferably a Fleisch-type or Lilly-type pneumotachometer. The gas flow meter can operate by measuring the differential pressure across or the bypass flow rate through a bypass around a laminar flow element, or the device may further comprise a differential pressure transducer that is capable of measuring the pressure drop across the flow meter, and a signal conditioner connected to the differential pressure transducer and capable of amplifying the signal and sending the signal to the computer.

In one aspect, the invention provides a method for using such a diagnostic device to measure the rate and size of particle exhalation in an individual by placing the mouthpiece in or over the individual's mouth or nose, inhaling air through the mouthpiece, wherein the air is pulled through the filter prior to inhalation, exhaling through the mouthpiece and into the one-way valve, measuring the number of particles and size of particles using the particle counter, and providing the data from the particle counter to the computer. The air is pulled through the gas flow meter during inhalation prior to being pulled through the filter. Data may be provided from the signal conditioner to the computer prior to exhalation through the mouthpiece. The steps of inhaling, exhaling, measuring, and providing data are often repeated multiple times and the mean particle size, average particle distribution, and mean rate of particle production are calculated. The method further can comprise inhaling a formulation that, when administered to the mucosal lining of a human or other animal, alters the surface viscoelastic properties of the mucosal lining, surface tension of the mucosal lining, or bulk viscosity of the mucosal lining, and then repeating the steps of placing the mouthpiece over the individual's mouth or nose, inhaling air through the mouthpiece, exhaling through the mouthpiece, measuring number and size of particles using the particle counter, providing the data from the particle counter to the computer, and calculating mean particle size, average particle distribution, and mean rate of particle production.

Formulations to reduce particle production are also described herein. The formulation is administered in an amount sufficient to alter biophysical properties in the mucosal linings of the body. When applied to mucosal lining fluids, the formulation alters the physical properties such as the gel characteristics at the air/liquid interface, surface elasticity, surface viscosity, surface tension and bulk viscoelasticity of the mucosal lining. The formulation is administered in an effective amount to minimize ambient contamination due to particle formation during breathing, coughing, sneezing, or talking, which is particularly important in the cleanroom applications. In one embodiment, the formulation for administration is a non-surfactant solution. In one embodiment, the formulations are conductive formulations containing conductive agents, such as salts, ionic surfactants, or other substances that are in an ionized state or easily ionized in an aqueous or organic solvent environment. One or more active agents, such as antivirals, antimicrobials, anti-inflammatories, proteins or peptides, may be included with the formulation.

BRIEF DESCRIPTION OF THE DRAWINGS

FIGS. 3A and 3B are illustrations of the preferred embodiment of the diagnostic instrument. In FIG. 3A, the lid is transparent. In FIG. 3B, the lid has been removed.

FIGS. 4A and 4B are illustrations of a preferred embodiment of the disposable kit. FIG. 4A is a space-filled illustration. FIG. 4B is a side-view FIGS. 5A and 5B are illustrations of a preferred embodiment of the mouthpiece. FIG. 5A is a front elevational view. FIG. 5B is a side view.

FIG. 6A is a space-filed view. FIG. 6B is a top view.

FIGS. 7A and 7B are illustrations of a preferred embodiment of the lid of the main housing. FIG. 7A is a view of the outside of the lid. FIG. 7B is a side view.

FIGS. 8A, 8B, and 8C are illustrations of a preferred embodiment of the flow meter. FIG. 8A is a space-filed view. FIGS. 8B and 8C are a side views.

FIGS. 9A, 9B and 9C illustrate particle concentration following three coughs measured over time for plain mucus simulant and following saline delivery at $t=0$ (FIG. 9A), $t=30$ (FIG. 9B) and $t=60$ minutes (FIG. 9C).

FIG. 13 is a graph of time following completion of administration of formulation for reduction of particle production (hours) versus average particle counts greater than 0.3 µm produced relative to baseline (% counts/liter).

DETAILED DESCRIPTION OF THE INVENTION

Lung mucociliary clearance is the primary mechanism by which the airways are kept clean from particles present in the liquid film that coats them. The conducting airways are lined with ciliated epithelium that beat to drive a layer of mucus towards the larynx, clearing the airways from the lowest ciliated region in 24 hours. The fluid coating consists of water, sugars, proteins, glycoproteins, and lipids. It is generated in the airway epithelium and the submucosal glands, and the thickness of the layer ranges from several microns in the trachea to approximately 1 micron in the distal airways in humans, rat, and guinea pig.

A second important mechanism for keeping the lungs clean is via momentum transfer from the air flowing through the lungs to the mucus coating. Coughing increases this momentum transfer and is used by the body to aid the removal of excess mucus. It becomes important when mucus cannot be adequately removed by ciliary beating alone, as occurs in mucus hypersecretion associated with many disease states.

Air speeds as high as 200 m/s can be generated during a forceful cough. The onset of unstable sinusoidal disturbances at the mucus layer has been observed at such air speeds. This disturbance results in enhanced momentum transfer from the air to the mucus and consequently accelerates the rate of mucus clearance from the lungs. Experiments have shown that this disturbance is initiated when the air speed exceeds some critical value that is a function of film thickness, surface tension, and viscosity (M. Gad-El-Hak, R. F. Blackwelder, J. J. Riley. *J. Fluid Mech.* (1984) 140:257-280). Theoretical predictions and experiments with mucus-like films suggest that the critical speed to initiate wave disturbances in the lungs is in the range of 5-30 m/s.

It is clear from the discussion above relating to cleanrooms that it would be highly advantages to (1) determine that rate of particle production and size range of particles produced by individuals, (2) predict which people will produce the greatest level of contamination and (3) minimize contamination produced by breathing, coughing, moving, etc.

The objectives can be achieved using a device such as that described herein which measures the size and number of particles produced on an individual basis. Particle production can be measured at rest or during various activities. This allows for determination if a formulation for reducing particle exhalation should be administered to an individual and/or for selection of individuals with the minimal particle production for use in cleanroom environments.

Figure 1:
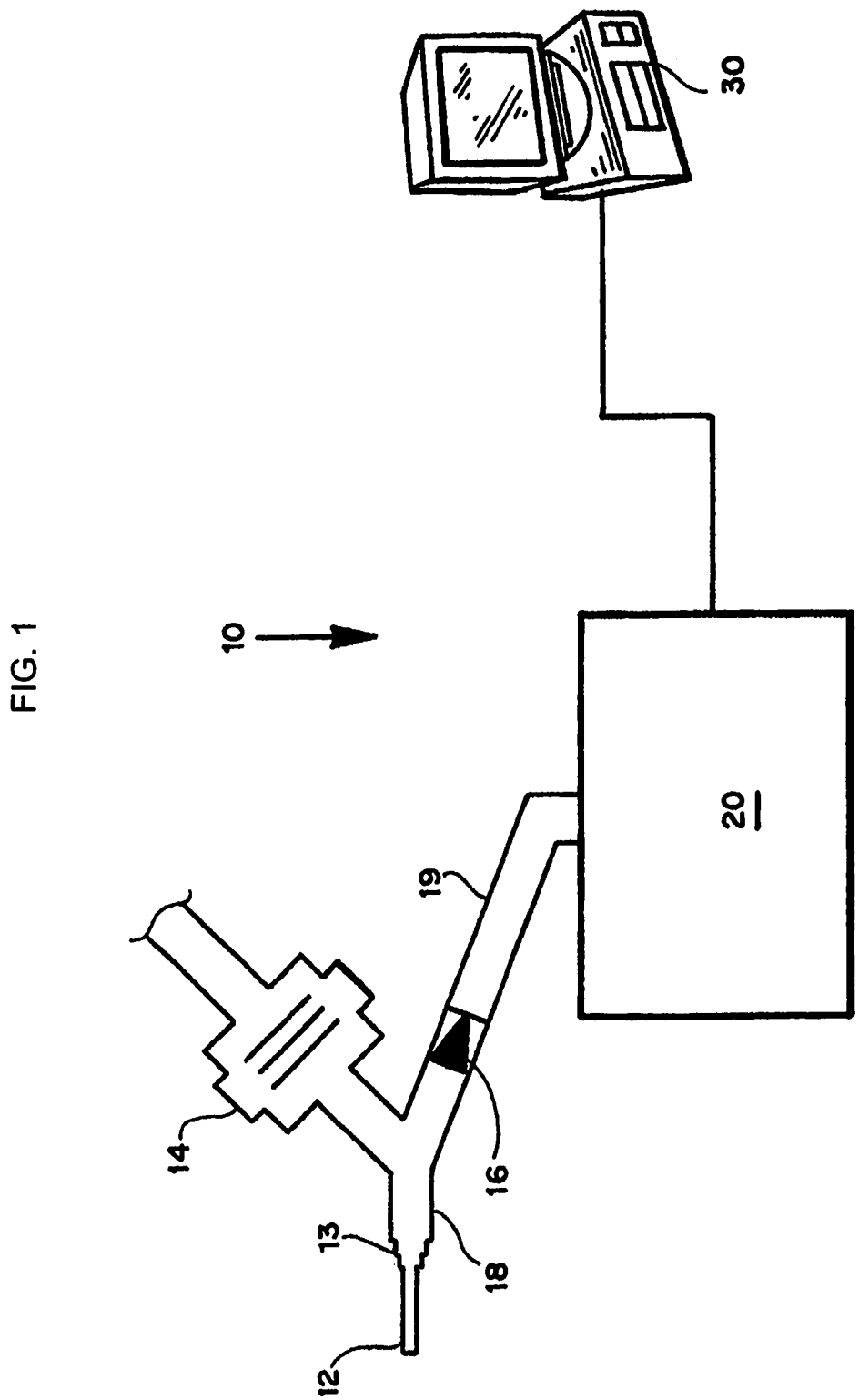
FIG. 1 is a schematic of a diagnostic instrument for the measurement of particles produced and exhaled by a person.
Figure 2:
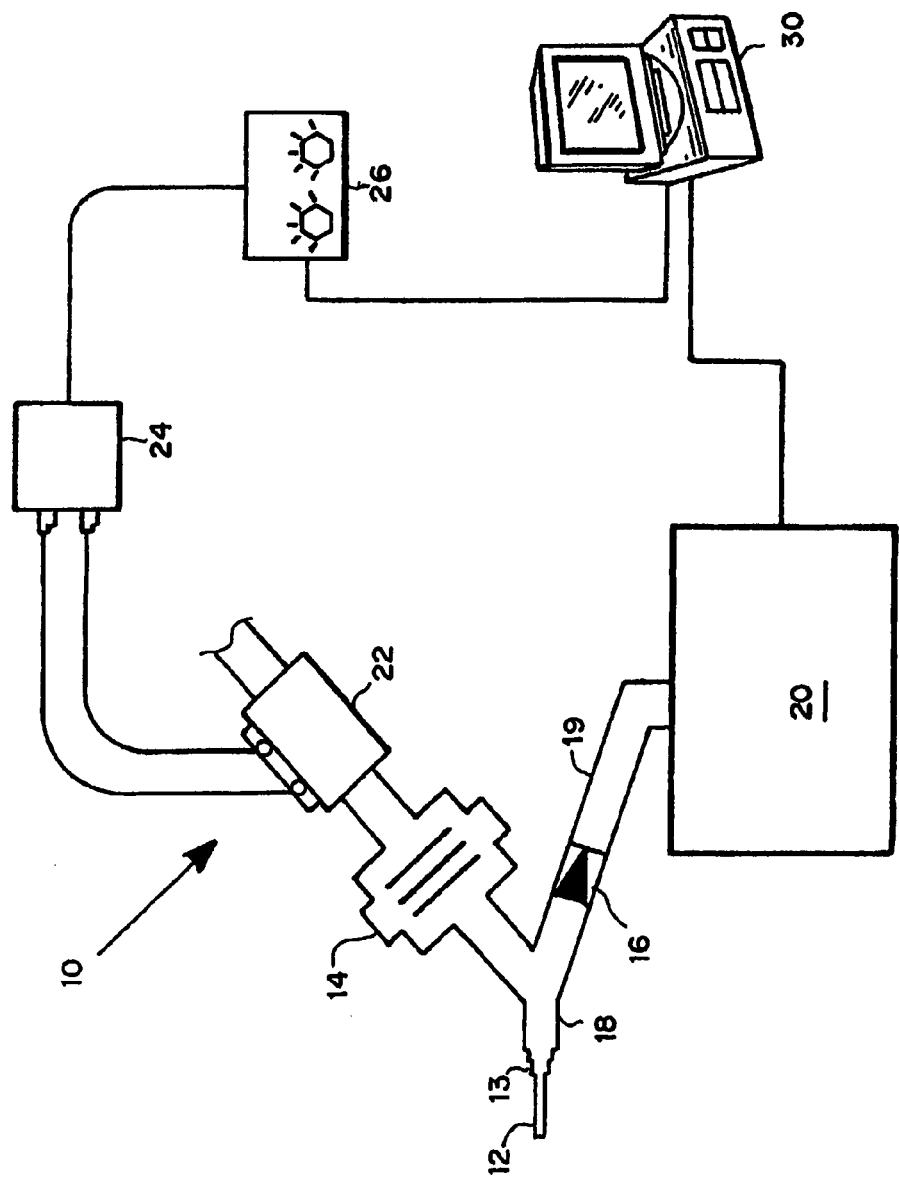
FIG. 2 is a schematic of a diagnostic instrument for the measurement of particles produced and exhaled by a person with associated breathing rate.

The first and second objections can be achieved using a device such as that described herein which measures the size and number of particles produced on an individual basis. Particle production can be measured at rest or during various activities. This allows for determination if a formulation for reducing particle exhalation should be administered to an individual and/or for selection of individuals with the minimal particle production for use in cleanroom environments.

The third objective can be achieved by administering a formulation for decreasing particle production, such as formulation containing a substances that are easily ionized in an aqueous or organic solvent environment (also referred to herein as "conductive agents"), as described herein. In one embodiment, the formulation is administered to one or more individuals using a device which provides an aerosol that sprays a fine mist of the formulation into the pulmonary and/or nasal region of an individual, thereby decreasing the output of particles. Individuals may be treated prior to entering, and/or after entering, the cleanroom.

I. Diagnostic Device for Determining Particle Production (Rate and Size Range)

Diagnosis of animals or humans to determine their rate of particle production and the size range of particles produced during exhalation. The analysis of this data can be used to determine if a formulation for reducing particle exhalation is needed. This device is particularly useful prior to entry in a cleanroom or while a user is working in a cleanroom to ensure that the cleanroom standards are maintained. The device can also be used to identify animals and humans who have an enhanced propensity to exhale aerosols (referred to herein as "over producers", "super-producers", or "superspreaders"). This can be accomplished by screening for a number of factors including the measurement of expired air and inspired air, the assessment of exhaled particle numbers, the assessment of exhaled particle size, the assessment of tidal volume and respiratory frequency during sampling, and the assessment of viral and bacterial infectivity. The assessment of exhaled particle numbers is done at a respiratory flow rate of about 10 to about 120 liters per minutes (LPM).

A diagnostic instrument (10) for the measurement of particles produced and exhaled by a person is illustrated in FIGS. 1-3. As shown in FIG. 1, the device (10) contains a mouthpiece (12). The outlet (13) of the mouthpiece (12) is attached to a filter (14) and a low resistance one-way valve (16) via a branched connector (18), such as a wye or tee connector. The one-way valve (16) is typically located inside a tube (19) which forms one half of the connector (18) or is attached directly to one end of the connector (18). At an end distal to the outlet (13) of the mouthpiece, the tube (19) is attached to a particle counter (20). The particle counter (20) is connected to the computer (30) in a manner that allows data to be provided to the computer (30). The data from the particle counter (20) is sent to a computer (30), to allow a user to read, analyze and interpret the data. In one embodiment the device is portable and, optionally, operates on batteries.

Any suitable mouthpiece may be used. In one embodiment, illustrated in FIGS. 1 and 2, the mouthpiece (12) is designed to allow the user to place his lips around the outside of the mouthpiece and thereby form a seal between his lips and the mouthpiece. In another embodiment, the mouthpiece is in the form of a nasal prongs and a seal is formed between the user's nostrils and the prongs. In another embodiment, the mouthpiece is in the form of a mask, which covers the user's mouth and nose. In this embodiment, a seal is formed between the user's face and the mask. In another embodiment, the mouthpiece is in the form of a mask which only covers the user's nose. Preferably the mouthpiece is disposable.

As shown in FIG. 3, the device (10) contains at least two main components: (1) a disposable kit (50) and a main housing (60). In the preferred embodiment, the disposable kit (50) is connected to the main housing (60) with one or more connecting tubes (70A and 70B) exterior to the main housing.

In a preferred embodiment, the mouthpiece (12), filter (14), connector (18), and one-way valve (16) are all disposable. Optionally, the mouthpiece (12), filter (14), connector (18), and/or one-way valve (16) are formed from biodegradable materials.

A. Disposable Kit

The disposable kit (50) is illustrated in FIGS. 4A and 4B. The disposable kit contains: a mouthpiece (12), a filter (14), a connector (18), and a one-way valve (16). In a preferred embodiment, the mouthpiece (12), filter (14), connector (18), and one-way valve (16) are all disposable. Optionally, the mouthpiece (12), filter (14), connector (18), and/or one-way valve (16) are formed from biodegradable materials.

The outlet (13) of the mouthpiece (12) is attached to a filter (14) and a low resistance one-way valve (16) via a branched connector (18), such as a wye or tee connector. The one-way valve (16) is typically located inside a tube (19) which forms one half of the connector (18) or is attached directly to one end of the connector (18). As shown in FIG. 3, the disposable kit is attached to the main housing (60) using one or more connecting tubes. In the embodiment illustrated by FIG. 3, two connecting tubes are used (70A and 70B).

i. Mouthpiece

Any suitable mouthpiece may be used. A preferred mouthpiece is illustrated in FIGS. 4A, 4B, 5A, and 5B. As shown in FIGS. 5A and 5B, the preferred mouthpiece is made of a flexible material, such as plastic, rubber, silicon (e.g., silicone rubber, polyvinyl chloride or thermoplastic rubber) or similar flexible material, and has a curved flange (40). When used, the curved flange (40) is placed between the user's lips and teeth to form a seal. The mouthpiece (12) has at least 2 protrusions (42A and 42 B) attached to the each of the opposite sides of the curved flange (40) and designed to fit between the user's top and bottom teeth to hold the mouthpiece in place when in use. When in use, the protrusions (42A and 42B) also function to set a gap between the top and bottom rows of teeth, ensuring that the user's mouth remains open throughout the use of the diagnostic device. It is preferred that the thickness of the protrusions is greater than 4 mm, most preferably between 6 and 15 mm. The curved flange (40) contains an opening (43) in the center of the flange. The flange is connected to a tube (44) through the opening (43). The opening (43) is located at the end (45) of the tube (44) proximal to the flange (40). The mouthpiece outlet (13) is located at the end (47) of the tube (44) that is distal to the flange (40). As illustrated in FIGS. 1 and 2, the mouthpiece (12) is designed to allow the user to place his lips around the outside of the mouthpiece and thereby form a seal between his lips and the mouthpiece. Alternatively, the mouthpiece is in the form of a nasal prongs and a seal is formed between the user's nostrils and the prongs. The mouthpiece may also be in the form of a mask, which covers the user's mouth and nose, with a seal formed between the user's face and the mask. Alternatively, the mouthpiece is in the form of a mask which only covers the user's nose. Preferably the mouthpiece is disposable.

ii. Filter

The filter (14) is typically a high efficiency (>99.97% at 0.3 µm), low pressure drop (<2.5 cm $H_2O$ at 60 L/min) filter, optionally the filter has a bacterial/viral removal efficiency of >99.99%. The filter is selected to remove at least particles having sizes in the range to be measured by the particle counter (20), preferably the filter removes particles having a sizes even smaller that the range to be measured by the particle counter. Preferably, the filter is designed to remove particles of greater than or equal to 0.1 micrometer in diameter. A series of two or more filters (14) may be included between the mouthpiece (12) and the ambient air in order to prevent the contamination of the upstream system between users. In this embodiment, one or more of the filters may be replaced with a bank of filters in parallel in order to minimize flow resistance. In a preferred embodiment illustrated in FIG. 3, the instrument contains two filters in series. The first filter (14) is external to the main housing and is part of the disposable kit (50). The second filter is internal to the main housing.

B. Main Housing

Figure 6A:
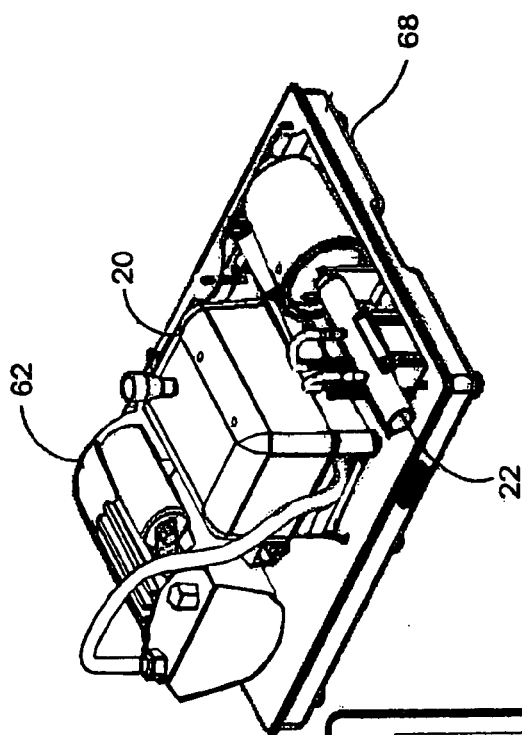
FIGS. 6A and 6B are illustrations of a preferred embodiment of the components attached to the bottom of the main housing.
Figure 6B:
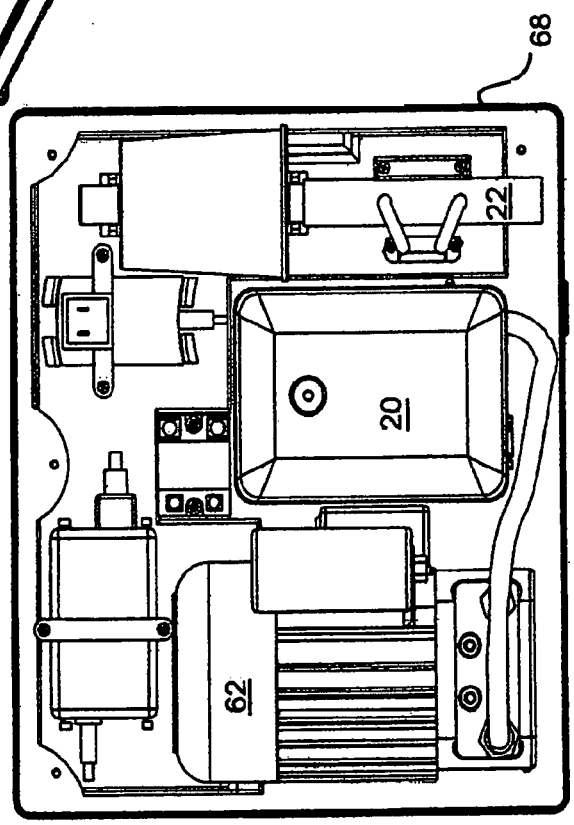

A preferred embodiment of the main housing (60) is illustrated in FIGS. 6A, 6B, 7A, and 7B. Preferably the main housing (60) contains a particle counter (20), a computer (30) and a vacuum pump (62), and a display (64). As shown in FIGS. 6A and 6B, the particle counter (20) and the vacuum pump (62) are attached to the bottom (68) of the main housing (60). As shown in FIG. 7B, the computer (30) is attached to the lid (66) of the main housing (60); and the display (64) is on the outside face of the lid (66).

The particle counter (20) is connected to the computer (30) in a manner that allows data to be provided to the computer (30). The data from the particle counter (20) is sent to a computer (30), to allow a user to read, analyze and interpret the data. As illustrated in FIGS. 6A and 6B, the particle counter (20) is connected to vacuum pump (62). Alternatively, the main housing contains the particle counter (20), but the computer (30), display (64) and/or vacuum pump (62) are exterior to the main housing.

i. Particle Counter

The particle counter (20) must have sufficient sensitivity to accurately count sub-micron sized particles and may be designed and assembled as described. The measurement of particle number and particle size can be done by electrical mobility analysis, impaction, electrostatic impaction, infrared spectroscopy, laser diffraction, or light scattering. Examples of currently available particle counters for the measurement of particle number and size include: Scanning Mobility Particle Sizer (SMPS) (TSI, Shoreview Minn.), Andersen cascade impactor or Next generation pharmaceutical impactor (Copley Scientific, Nottingham UK), Electrical low pressure impactor (ELPI) (Dekati, Tampere Finland) and Helos (Sympatec, Clausthal, Germany). In a preferred embodiment, the particle counter is an optical particle counter, most preferably one which operated by light scattering using a LASER or laser diode light source. The optical particle counter normally has a range of at least 0.3 to 5 µm and preferably from 0.1 to 25 µm, and differentiates its measurement range into at least 2 channels and preferably at least 4 channels. The optical particle carrier can operate at a steady sample flow rate of at least 0.1 cubic foot per minute and preferably of at least 1 cubic foot per minute which may be generated and controlled as part of the particle counter or as separate vacuum pump (62) and flow regulator components. Currently available optical particle counters that may be appropriate for this preferred embodiment include model CI-450, CI-500, CI-550 of Ultimate 100 (Climet Instruments, Redlands Calif.) and models Lasair II, Airnet 310, (Particle Measuring Systems, Boulder Colo.).

ii. Computer

The particle counter (20) is connected to the computer (30) in a manner that allows data from the particle counter (20) to be sent to the computer (30). Optionally, the particle counter (20) is also connected to the computer (30) in a manner that allows control commands to be sent from the computer (30) to the particle counter (20). The computer may be a microprocessor internal or external to the particle counter. Preferably, the computer includes a display which may be physically separated from the central processing and data storage units and more preferably the display incorporates touch screen capabilities. As shown in FIGS. 3A and 3B, in a preferred embodiment, the main housing (60) contains the particle counter (20) and the computer (30 iii. Flow Meter

As illustrated in FIG. 2, the device (10) may contain a gas flow meter (22). The gas flow meter (22) should have a low flow resistance so as not to influence the user's respiration rate such as a pneumotachometer or pneumotachograph of type Fleisch or Lilly. Alternatively, the gas flow meter may measure flow by measuring the temperature change or heat transfer from an electrically heated wire (e.g., a hot wire anemometer), or by counting the number of revolutions per unit of time of a small turbine (e.g., a turbine flow meter), or by measuring the differential pressure across or the bypass flow rate through a bypass around a flow restriction, such as a laminar flow element. The volume displacement may then be computed by integrating flow with respect to time.

Pneumotachometers are commonly used to measure the flow rate of different gases during respiration. Air is passed through a short tube (e.g., a Fleisch tube) that contains a mesh which presents a small resistance to the air flow (not shown in figure). The resulting pressure drop across the mesh is proportional to the flow rate. The pressure drop is very small, usually around a few $mmH_2O$. A differential pressure transducer (24) is normally used to measure the pressure drop across the flow meter (e.g. Fleisch tube), in order to enhance detection of such small drops in pressure. Preferably the differential pressure transducer is connected to a signal conditioner (26) which amplifies the signal and sends it to data acquisition software in the computer (30). One differential pressure transducer (24) useful in the invention is a Validyne DP45-14 differential pressure transducer. If this is used, the preferred signal conditioner (26) is a Validyne CD15 sine wave carrier demodulator. The pneumotachometer may be used in lung function analysis, or during artificial ventilation of the lungs.

As shown in FIGS. 8A-8C, the preferred flow meter contains a by-pass tube (82, a low flow rate flow meter (84), and a laminar flow element (86). Flow meter (22) is normally a low flow rate mass flow meter measuring the bypass flow around a flow restriction, such as a laminar flow element (86). The laminar flow element (86) consists of a series of parallel tubes sized such that the flow through the tubes is in the laminar flow regime for respirable flow rates, preferably for flow rates between +130 and −70 L/min, where positive flow represents the flow direction during exhalation. In a preferred embodiment, the low flow meter provides digital output at a frequency greater than 5 Hz. One example of this type of flow meter is the Sensirion model ASF1430.

C. Accessories

The device (10) often includes connections for performing further exhaled breath analysis simultaneously or in series with particle size and count measurements. For example, exhaled breath condensate may be collected in standard devices such as R-tubes or exhaled air may be passed through culture media filters for further analysis via connections (not shown in figure) located along the tube (19) leading to the optical particle counter (20).

II. Formulations for Decreasing Particle Production

Bioaerosol particles are formed by instabilities in the endogenous surfactant layer in the airways. The formulations described herein, for use in certain embodiments of the instant invention, are effective to alter the biophysical properties of the mucosal lining. These properties include, for example, increasing gelation at the mucus surface, the surface tension of the mucosal lining, the surface elasticity of the mucosal lining, and the bulk viscoelasticity of the mucosal lining. The formulations described herein are effective to decrease particle exhalation, by preventing or reducing exhaled particle formation from the oropharynx or nasal cavities. The endogenous surfactant layer may be altered by simply diluting the endogenous surfactant pool via either delivery of isotonic saline (though not in such a large amount as to cause a subject to expectorate) or a hypertonic saline solution that causes the cells lining the lung's airways to dilute further the endogenous surfactant layer via production of water.

It has been discovered that physical properties of the endogenous surfactant fluid in the lungs, can be altered by administration of a saline solution, as well as by administration of an aqueous saline solution containing other materials, such as osmotically active materials, conductive materials, and/or surfactants. Concentration ranges of the salt or other osmotically active material range from about 0.01% to about 10% by weight, preferably between 0.9% to about 10%. A preferred aerosol solution for altering physical properties of the mucosal lining is isotonic saline.

A. Conductive Formulations

Preferred formulations for altering the biophysical properties of the lung's lining fluid are formulations containing certain charge concentrations and mobility, and thus liquid conductivity. In one preferred embodiment, the formulations include aqueous solutions or suspensions that are conductive (also referred to herein as the "conductive formulation(s)"). Suitable conductive formulations typically have conductivity values of greater than 5,000 µS/cm, preferably greater than 10,000 µS/cm, and more preferably greater than 20,000 µS/cm. These formulations are particularly useful when administered to a patient to suppress particle exhalation. Solution conductivity is a product of the ionic strength, concentration, and mobility (the latter two contribute to the conductivity of the formulation as a whole). Any form of the ionic components (anionic, cationic, or zwitterionic) can be used. These conductive materials may alter the mucosal lining properties by acting, for example, as a cross-linking agent within the mucus. The ionic components in the formulations described herein may interact with the strongly linked anionic glycoproteins within normal tracheobronchial mucus. These interactions may influence the state of the air/liquid surface of the airway lining fluid and transiently the nature of the physical entanglements due to covalent and noncovalent interactions, including hydrogen bonding, hydrophobic, and electrostatic interactions (Dawson, M., Wirtz, D., Hanes, J. (2003) The Journal of Biological Chemistry. Vol. 278, No. 50, pp. 50393-50401).

Optionally the formulation includes mucoactive or mucolytic agents, such as MUC5AC and MUC5B mucins, DNA, N-acetylcysteine (NAC), cysteine, nacystelyn, dornase alfa, gelsolin, heparin, heparin sulfate, P2Y2 agonists (e.g. UTP, INS365), and nedocromil sodium.

Certain formulations of the invention contain substances that are easily ionized in an aqueous or organic solvent environment (also referred to herein as "conductive agents"), such as salts, ionic surfactants, charged amino acids, charged proteins or peptides, or charged materials (cationic, anionic, or zwitterionic). Suitable salts include any salt form of the elements sodium, potassium, magnesium, calcium, aluminum, silicon, scandium, titanium, vanadium, chromium, cobalt, nickel, copper, manganese, zinc, tin, and similar elements. Examples include sodium chloride, sodium acetate, sodium bicarbonate, sodium carbonate, sodium sulfate, sodium stearate, sodium ascorbate, sodium benzoate, sodium biphosphate, sodium phosphate, sodium bisulfite, sodium citrate, sodium borate, sodium gluconate, calcium chloride, calcium carbonate, calcium acetate, calcium phosphate, calcium alginate, calcium stearate, calcium sorbate, calcium sulfate, calcium gluconate, magnesium carbonate, magnesium sulfate, magnesium stearate, magnesium trisilicate, potassium bicarbonate, potassium chloride, potassium citrate, potassium borate, potassium bisulfite, potassium biphosphate, potassium alginate, potassium benzoate, magnesium chloride, cupric sulfate, chromium chloride, stannous chloride, and sodium metasilicate and similar salts. Suitable ionic surfactants include sodium dodecyl sulfate (SDS) (also known as sodium lauryl sulfate (SLS)), magnesium lauryl sulfate, Polysorbate 20, Polysorbate 80, and similar surfactants. Suitable charged amino acids include L-Lysine, L-Arginine, Histidine, Aspartate, Glutamate, Glycine, Cysteine, Tyrosine. Suitable charge proteins or peptides include proteins and peptides containing the charged amino acids, Calmodulin (CaM), and Troponin C. Charged phospholipids, such as 1,2-dioleoyl-sn-glycero-3-ethylphosphocholine triflate (EDOPC) and alkyl phosphocholine trimesters, can be used.

The preferred formulations are formulations containing salts, such as saline (0.15 M NaCl or 0.9%) solution, $CaCl_2$ solution, $CaCl_2$ in saline solution, or saline solution containing ionic surfactants, such as SDS or SLS. In certain embodiments, the formulation contains saline solution and $CaCl_2$. Suitable concentration ranges of the salt or other conductive/charged compounds can vary from about 0.01% to about 20% (weight of conductive or charged compound/total weight of formulation), preferably between 0.1% to about 10% (weight of conductive or charged compound/total weight of formulation), most preferably between 0.1 to 7% (weight of conductive or charged compound/total weight of formulation).

Saline solutions have long been delivered chronically to the lungs with small amounts of therapeutically active agents, such as beta agonists, corticosteroids, or antibiotics. For example, VENTOLIN® Inhalation Solution (GSK) is an albuterol sulfate solution used in the chronic treatment of asthma and exercise-induced bronchospasm symptoms. A VENTOLIN® solution for nebulization is prepared (by the patient) by mixing 1.25-2.5 mg of albuterol sulfate (in 0.25-0.5 mL of aqueous solution) into sterile normal saline to achieve a total volume of 3 mL. No adverse effects are thought to be associated with the delivery of saline to the lungs by VENTOLIN® nebulization, even though nebulization times can range from 5-15 minutes. Saline is also delivered in more significant amounts to induce expectoration. Often these saline solutions are hypertonic (sodium chloride concentrations greater than 0.9%, often as high as 5%) and generally they are delivered for up to 20 minutes.

B. Osmotically Active Materials

Many materials may be osmotically active, including binary salts, such as sodium chloride, or any other kinds of salts, or sugars, such as mannitol. Osmotically active materials, normally owing to their ionization and possibly size, do not easily permeate cell membranes and therefore exert an osmotic pressure on contiguous cells. Such osmotic pressure is essential to the physical environment of cellular material, and regulation of this pressure occurs by cell pumping of water into or out of the cell. Solutions delivered to the lungs that are isotonic normally do not create an imbalance in osmotic pressure in the lung fluid and therefore simply dilute the natural endogenous lung fluid with water and salt. Solutions of high osmotic content (i.e. hypertonic solutions) create an imbalance of osmotic pressure, with greater pressure in the lung fluid, causing cells to pump water into the lung fluid and therefore further dilute lung surfactant composition.

C. Active Ingredients

The formulations disclosed herein can be used by any route for delivery of a variety of organic or inorganic molecules, especially small molecule drugs, such as antivirals and antibacterial drugs including antibiotics, antihistamines, bronchodilators, cough suppressants, anti-inflammatories, vaccines, adjuvants and expectorants. Examples of macromolecules include proteins and large peptides, polysaccharides and oligosaccharides, and DNA and RNA nucleic acid molecules and their analogs having therapeutic, prophylactic or diagnostic activities. Nucleic acid molecules include genes, antisense molecules that bind to complementary DNA to inhibit transcription, and ribozymes. Preferred agents are antiviral, steroid, bronchodilators, antibiotics, mucus production inhibitors and vaccines.

In the preferred embodiment, the concentration of the active agent ranges from about 0.01% to about 20% by weight. In a more preferred embodiment, the concentration of active agent ranges from between 0.9% to about 10%.

D. Carriers and Aerosols for Administration

The formulation may be delivered in a solution, a suspension, a spray, a mist, a foam, a gel, a vapor, droplets, particles, or a dry powder form (for example, using a metered dose inhaler including HFA propellant, a metered dose inhaler with non-HFA propellant, a nebulizer, a pressurized can, or a continuous sprayer). Carriers can be divided into those for administration via solutions or suspensions (liquid formulations) and those for administration via particles (dry powder formulations).

1. Dosage Forms for Administration to Different Mucosal Surfaces

For administration to mucosal surfaces in the respiratory tract, the formulation is typically in the form of solution, suspension or dry powder. Preferably, the formulation is aerosolized. The formulation can be generated via any aerosol generators, such as dry powder inhaler (DPI), nebulizers or pressurized metered dose inhalers (pMDI). The term "aerosol" as used herein refers to any preparation of a fine mist of particles, typically less than 10 microns in diameter. The preferred mean diameter for aqueous formulation aerosol particles is about 5 microns, for example between 0.1 and 30 microns, more preferably between 0.5 and 20 microns and most preferably between 0.5 and 10 microns.

For administration to the oral mucosa, including buccal mucosa, the formulation may be administered as a solid that dissolves following administration to the mouth and/or adheres to the mucosal surface, or a liquid.

A preferred aerosol solution for altering physical properties of the lung's lining fluid is isotonic saline. The aerosol can consist just of a solution, such as an aqueous solution, most preferably a saline solution. Alternatively, the aerosol may consist of an aqueous suspension or dry particles.

2. Liquid Formulations

Aerosols for the delivery of therapeutic agents to the respiratory tract have been developed. See, for example, Adjei, A. and Garren, *J. Pharm. Res.,* 7: 565-569 (1990); and Zanen, P. and Lamm, J.-W. *J. Int. J. Pharm.,* 114: 111-115 (1995). These are typically formed by atomizing a liquid formulation, such as a solution or suspension, under pressure through a nebulizer or through the use of a metered dose inhaler ("MDI"). In the preferred embodiment, the liquid formulations are aqueous solutions or suspensions.

3. Dry Powder Formulations

The geometry of the airways is a major barrier for drug dispersal within the lungs. The lungs are designed to entrap particles of foreign matter that are breathed in, such as dust. There are three basic mechanisms of deposition: impaction, sedimentation, and Brownian motion (J. M. Padfield. 1987. In: D. Ganderton & T. Jones eds. Drug Delivery to the Respiratory Tract, Ellis Harwood, Chicherster, U.K.). Impaction occurs when particles are unable to stay within the air stream, particularly at airway branches. They are adsorbed onto the mucus layer covering bronchial walls and cleaned out by mucocilliary action. Impaction mostly occurs with particles over 5 μm in diameter. Smaller particles (<5 μm) can stay within the air stream and be transported deep into the lungs. Sedimentation often occurs in the lower respiratory system where airflow is slower. Very small particles (<0.6 μm) can deposit by Brownian motion. This regime is undesirable because deposition cannot be targeted to the alveoli (N. Worakul & J. R. Robinson. 2002. In: Polymeric Biomaterials, $2^{nd}$ ed. S. Dumitriu ed. Marcel Dekker. New York).

The preferred mean diameter for aerodynamically light particles for inhalation is at least about 5 microns, for example between about 5 and 30 microns, most preferably between 3 and 7 microns in diameter. The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different therapeutic agent may be administered to target different regions of the lung in one administration.

As used herein, the phrase "aerodynamically light particles" refers to particles having a mean or tap density less than about 0.4 $g/cm^3$. The tap density of particles of a dry powder may be obtained by the standard USP tap density measurement. Tap density is a standard measure of the envelope mass density. The envelope mass density of an isotropic particle is defined as the mass of the particle divided by the minimum sphere envelope volume in which it can be enclosed. Features contributing to low tap density include irregular surface texture and porous structure.

Dry powder formulations ("DPFs") with large particle size have improved flowability characteristics, such as less aggregation (Visser, J., *Powder Technology* 58: 1-10 (1989)), easier aerosolization, and potentially less phagocytosis. Rudt, S, and R. H. Muller, *J. Controlled Release*, 22: 263-272 (1992); Tabata, Y., and Y. Ikada, *J. Biomed. Mater. Res.*, 22: 837-858 (1988). Dry powder aerosols for inhalation therapy are generally produced with mean diameters primarily in the range of less than 5 microns, although a preferred range is between one and ten microns in aerodynamic diameter. Ganderton, D., *J. Biopharmaceutical Sciences*, 3:101-105 (1992); Gonda, I. "Physico-Chemical Principles in Aerosol Delivery," in Topics in Pharmaceutical Sciences 1991, Crommelin, D. J. and K. K. Midha, Eds., Medpharm Scientific Publishers, Stuttgart, pp. 95-115 (1992). Large "carrier" particles (containing no drug) have been co-delivered with therapeutic aerosols to aid in achieving efficient aerosolization among other possible benefits. French, D. L., Edwards, D. A. and Niven, R. W., *J. Aerosol Sci.*, 27: 769-783 (1996). Particles with degradation and release times ranging from seconds to months can be designed and fabricated by established methods in the art.

Particles can contain conductive agent(s), alone, or in combination with drug, antiviral, antibacterial, antimicrobial, surfactant, proteins, peptides, polymer, or combinations thereof. Representative surfactants include L-α.-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty acids, sorbitan trioleate (Span 85), glycocholate, surfactin, poloxomers, sorbitan fatty acid esters, tyloxapol, phospholipids, and alkylated sugars. Polymers may be tailored to optimize particle characteristics including: i) interactions between the agent to be delivered and the polymer to provide stabilization of the agent and retention of activity upon delivery; ii) rate of polymer degradation and thus drug release profile; iii) surface characteristics and targeting capabilities via chemical modification; and iv) particle porosity. Polymeric particles may be prepared using single and double emulsion, solvent evaporation, spray drying, solvent extraction, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the conductive/charged materials, spraying the solution onto a substrate to form droplets of the desired size, and removing the solvent.

III. Administration of Formulations to the Respiratory Tract

A. Administration of Conductive Formulations to Reduce Amount of Exhaled Particles A conductive formulation can be administered that contains a suitable conductivity for increasing the viscoelasticity of the mucosal membrane at the site of administration of the formulation to suppress or reduce the formation of bioaerosol particles formation during breathing, coughing, sneezing, and/or talking. Preferably, the formulation is administered to one or more individuals in an effective amount to reduce particle production. The formulation may be administered to a person prior to entry in a cleanroom or while a person is working in a cleanroom to ensure that the cleanroom standards are maintained. If animals or humans have been identified as having an enhanced propensity to exhale aerosols (i.e., are "over producers", "super-producers", or "super-spreaders"), the formulation may be administered to reduce particle production, to prevent or reduce spread of infections, or to prevent or reduce uptake of pathogens by the human or animal.

B. Administration to the Respiratory Tract

The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. J. S. Patton & R. M. Platz. 1992. *Adv. Drug Del. Rev.* 8:179-196

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which lead to the ultimate respiratory zone, the alveoli or deep lung. The deep lung, or alveoli, is the primary target of inhaled therapeutic aerosols for systemic drug delivery.

The formulations are typically administered to an individual to deliver an effective amount to alter physical properties such as surface tension and viscosity of endogenous fluid in the upper airways, thereby enhancing delivery to the lungs and/or suppressing coughing and/or improving clearance from the lungs. Effectiveness can be measured using a diagnostic device as described herein. For example, saline can be administered in a volume of 1 gram to a normal adult. Exhalation of particles is then measured. Delivery is then optimized to minimize dose and particle number.

Formulations can be administered using a metered dose inhaler ("MDI"), a nebulizer, an aerosolizer, or using a dry powder inhaler. Suitable devices are commercially available and described in the literature.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6:273-313, 1990; and in Moren, "Aerosol dosage forms and formulations," in: Aerosols in Medicine, Principles, Diagnosis and Therapy, Moren, et al., Eds. Esevier, Amsterdam, 1985.

Delivery is achieved by one of several methods, for example, using a metered dose inhaler including HFA propellant, a metered dose inhaler with non-HFA propellant, a nebulizer, a pressurized can, or a continuous sprayer. For example, the patient can mix a dried powder of pre-suspended therapeutic with solvent and then nebulize it. It may be more appropriate to use a pre-nebulized solution, regulating the dosage administered and avoiding possible loss of suspension. After nebulization, it may be possible to pressurize the aerosol and have it administered through a metered dose inhaler (MDI). Nebulizers create a fine mist from a solution or suspension, which is inhaled by the patient. The devices described in U.S. Pat. No. 5,709,202 to Lloyd, et al., can be used. An MDI typically includes a pressurized canister having a meter valve, wherein the canister is filled with the solution or suspension and a propellant. The solvent itself may function as the propellant, or the composition may be combined with a propellant, such as FREON® (E.I. Du Pont De Nemours and Co. Corp.). The composition is a fine mist when released from the canister due to the release in pressure.

The propellant and solvent may wholly or partially evaporate due to the decrease in pressure.

Alternatively, the formulation is in the form of salt or osmotically active material particles which are dispersed on or in an inert substrate, which is placed over the nose and/or mouth and the formulation particles inhaled. The inert substrate is preferably a biodegradable or disposable woven or non-woven fabric and more preferably the fabric is formed of a cellulosic-type material. An example is tissues currently sold which contain lotion to minimize irritation following frequent use. These formulations can be packaged and sold individually or in packages similar to tissue or baby wipe packages, which are easily adapted for use with a liquid solution or suspension.

The formulation may be administered to one or more individuals using a device which provides an aerosol that sprays a fine mist of the formulation into the pulmonary and/or nasal region of an individual, thereby decreasing the output of particles. The formulation may be administered to humans or animals by creating an aqueous environment in which the humans and animals move or remain for sufficient periods of time to sufficiently hydrate the lungs. This atmosphere might be created by use of a nebulizer or even a humidifier. Preferably the nebulizer or humidifier administers a conductive formulation. Individuals may be treated prior to entering, and/or after entering, a cleanroom.

IV. Methods of Using the Diagnostic Device

When using the device illustrated in FIGS. 1 and 2, the user places his lips around the mouthpiece (12). The user seals his airways off from the ambient air preferably via a nose clip and by sealing his lips to a mouthpiece. If a mask is used as the mouthpiece, the user places the mask over his mouth and/or nose. If nose prongs are used as the mouthpiece, the user places the nose prongs in his nose. If the mouthpiece is in the form of a mask, the user places the mask over his nose and/or mouth, and thereby seals off his airways from the ambient air.

When using the device illustrated in FIGS. 3-8, the user places the curved flange (40) between his lips and teeth to form a seal. The user bites down on the two protrusions (42A and 42 B) to hold the mouthpiece in place when in use and to keep his mouth open during use.

When the user inhales, inspired air enters the system through the filter (14) which removes particles in the predetermined measured range. Exhaled air passes through the low resistance one-way valve (16) and into the particle counter (20). The one-way valve (16) helps to prevent the transmission of exhaled pathogens from one user to the next.

The expired air travels to the particle counter (20), which measures the number of particles and size of particles. The particle counter (20) samples at a fixed flow rate preferably greater than the peak exhaled flow rate so that at all points in time the mean flow direction through the filter (14) is into the system, preventing the loss of exhaled particles into the filter (14). Preferably the particle counter samples at flow rates greater than 28 L/min. The particle counter (20) then provides the data to the computer (30). In one embodiment, the user is provided with a visual feedback of his breathing pattern and cues to maintain a prescribed breathing pattern, for example tidal breathing. The particle counter (20) can be controlled either remotely from a PC or locally such as from a touch screen interface (see FIG. 7A, element 64) with data measurement and analysis performed locally at the main housing or remotely at a personal computer. A controller for the generation and control of the sample flow rate may be internal or external to the main housing. The inhalation, exhalation, and measurement steps may be repeated multiple times. Then the computer calculates the mean particle size, the average particle distribution, and mean rate of particle production. If it is necessary to decrease the number and size of particles exhaled by the user, a formulation for decreasing particle exhalation, such as described in PCT/US2006/000618, filed Jan. 10, 2006, is administered to the user.

Optionally, the diagnostic instrument (10) is designed to measure particles produced and exhaled by a person with associated breathing rate. In this embodiment, illustrated in FIG. 2, the inspired air enters the system through a low flow resistance flow meter (22) which characterizes the breathing pattern of the user and the particle counter flow rate together. Air then enters the filter (14) which removes particles in the measured range. Exhaled air passes through a low resistance one way valve (16), through the tube (18) and into the particle counter (20), as described above. The data from the flow meter, differential pressure transducer, and or signal conditioner is sent to the computer for calculation and analysis.

Depending on the rate of particle production and size of particles produced, as determined by the data obtained using the diagnostic device, a formulation may be administered to the user in an effective amount to reduce particle production. The formulation may be administered prior to entry or following entry into a cleanroom.

Unless defined otherwise, all technical and scientific terms used herein have the same meanings as commonly understood by one of skill in the art to which the disclosed invention belongs. Publications cited herein and the material for which they are cited are specifically incorporated by reference.

The present invention will be further understood by reference to the following non-limiting examples.

EXAMPLES

Example 1

In Vitro Simulation

A simulated cough machine system was designed similar to that described by King Am. J. Respir. Crit. Care Med. 156(1):173-7 (1997). An air-tight 6.25-liter Plexiglas tank equipped with a digital pressure gauge and pressure relief valve was constructed to serve as the capacitance function of the lungs. To pressurize the tank, a compressed air cylinder with regulator and air filter was connected to the inlet. At the outlet of the tank, an Asco two-way normally-closed solenoid valve (8210G94) with a sufficient Cv flow factor was connected for gas release. The solenoid valve was wired using a typical 120V, 60 Hz light switch. Connected to the outflow of the solenoid valve was a Fleisch no. 4 pneumotachograph, which created a Poiseuille flow needed to examine the "cough" profile. The outlet of the Fleisch tube was connected to a ¼" NPT entrance to the model trachea. A Validyne DP45-14 differential pressure transducer measured the pressure drop through the Fleisch tube. A Validyne CD15 sine wave carrier demodulator was used to amplify this signal to the data acquisition software. Weak polymeric gels with rheological properties similar to tracheobronchial mucus were prepared as described by King et al Nurs Res. 31(6):324-9 (1982). Locust bean gum (LBG) (Fluka BioChemika) solutions were crosslinked with sodium tetraborate ($Na_2B_4O_7$) (J. T. Baker). LBG at 2% wt/vol was dissolved in boiling Milli-Q distilled water. A concentrated sodium tetraborate solution was prepared in Milli-Q distilled water. After the LBG solution cooled to room temperature, small amounts of sodium tetraborate solution were added and the mixture was slowly rotated for 1 minute. The still watery mucus simulant was then pipetted onto the model trachea creating simulant depth based on simple trough geometry. Mucus simulant layers were allowed 30 minutes to crosslink prior to initiation of "cough" experiments. At this point, t=0 min, time points were measured, followed by t=30 min and t=60 min. Final concentrations of sodium tetraborate ranged from 1-3 mM. An acrylic model trachea was designed 30 cm long with interior width and height of 1.6 cm. The model trachea formed a rectangular shaped tube with a separate top to fit, allowing for easy access to the mucus simulant layer. A gasket and C-clamps were used to create an air-tight seal. A rectangular cross-section was chosen to enable uniform mucus simulant height and to avoid problems associated with round tubes and gravity drainage. The cross-sectional area of the model trachea was also physiologically relevant. The end of the model trachea remained open to the atmosphere. Nebulized solutions were delivered to the mucus simulant via a PARI LC Jet nebulizer and Proneb Ultra compressor. Formulations included normal isotonic 0.9% saline (VWR) and 100 mg/mL of synthetic phospholipids 1,2-Dipalmitoyl-sn-glycero-3-phosphocholine/1-Palmitoyl-2-oleoyl-sn-glycero-3-phosphoglycerol (DPPC/POPG) (Genzyme) 7/3 wt % suspended in isotonic saline. 3 mL of the chosen formulation was pipetted into the nebulizer and aerosolized until nebulizer sputter through the open-ended but clamped model trachea trough on the layer of mucus simulant. The model trachea was then attached to the outlet of the Fleisch tube prior to t=0 min experiments. As well, t=30 min and t=60 min (post-dose) experiments were performed.

A Sympatec HELOS/KF laser diffraction particle sizer was used to size the created mucus simulant bioaerosols. The Fraunhoffer method for sizing diffracted particles was used. The HELOS was equipped with an R2 submicron window module enabling a measuring range of 0.25-87.5 µm. Prior to "cough" experiments, the end of the model trachea was adjusted to be no more than 3 cms from the laser beam. As well, the bottom of the model trachea was aligned with the 2.2 mm laser beam using support jacks and levels. Dispersed bioaerosols were collected after passing through the diffraction beam using a vacuum connected to an inertial cyclone followed by a HEPA filter. Before each run, the laser was referenced for 5 s to ambient conditions. Measurement began after a specified trigger condition of optical concentration $(C_{opt}) \geq 0.2\%$ and stopped 2 s after $C_{opt} \leq 0.2\%$. Sympatec WINDOX software was used to create cumulative and density distribution graphs versus log particle size by volume.

A typical cough profile, consisting of a biphasic burst of air, was passed over the 1.5 mm layer of mucus simulant. The initial flow or air possessed a flow rate of about 12 L/s for 30-50 ms. The second phase lasted 200-500 ms and then rapidly decayed.

Bioaerosol particle concentration following three coughs was measured over time (FIGS. 9A, 9B and 9C) in the case of an undisturbed mucus simulant, and in the cases of saline delivery (FIGS. 9A, 9B and 9C) and surfactant delivery (not shown). In the undisturbed case, bioaerosol particle size remains constant over time with a median size of about 400 nanometers. Following the addition of saline, bioaerosol particle size increases from 1 micron (t=0) (FIG. 9A) to about 60 microns (t=30 min) (FIG. 9B) and then diminishes to 30 microns (t=60 min) (FIG. 9C).

These in vitro results show that saline delivered to a mucus layer causes a substantial increase in particle size on breakup, possibly owing to an increase in surface tension. As indicated by the in vivo results, the larger size droplets are less capable of exiting the mouth. Therefore, delivery of the solution serves to significantly lower the number of expired particles.

Example 2

Reduction of Exhaled Aerosol Particles in Human Study

A proof of concept study of exhaled aerosol particle production was performed using 12 healthy subjects. The objectives of the study were (1) to determine the nature of exhaled bioaerosol particles (size distribution and number); (2) to validate the utility of a device that is sensitive enough to accurately count the exhaled particles; (3) to assess the baseline count of particles exhaled from the healthy lung; and (4) to measure the effect of two exogenously administered treatment aerosols on exhaled particle count suppression. Experiments were performed with different particle detectors to determine average particles per liter and average particle size for healthy human subjects. Following the inspiration of particle-free air, healthy subjects breathe out as little as 1-5 particles per liter, with an average size of 200-400 nm in diameter. Significant variations occur in numbers of particles from subject to subject, so that some subjects exhale as many as 30,000 particles per liter, again predominantly of submicron particle size. A device with sufficient sensitivity to accurately count sub-micron sized particles was designed and assembled. The LASER component of the device was calibrated in accordance with manufacturer procedures (Climet Instruments Company, Redlands, Calif.). This device accurately measured particles in the range of 150-500 nm with a sensitivity of 1 particle/liter. A series of filters eliminated all background particle noise.

Following protocol IRB approval, 12 healthy subjects were enrolled in the study. Inclusion criteria were good health, age 18-65 years, normal lung function ($FEV_1$ predicted>80%), informed consent and capability to perform the measurements. Exclusion criteria were presence or a history of significant pulmonary disease (e.g. asthma, COPD, cystic fibrosis), cardiovascular disease, acute or chronic infection of the respiratory tract, and pregnant or lactating females. One individual was not able to complete the entire dosing regimen and therefore was excluded from the data analysis.

Following a complete physical exam, the subjects were randomized into two groups: those to initially receive prototype formulation 1 and those to receive prototype formulation 2. Baseline exhaled particle production was measured after a two minute "wash out" period on the device. The assessment was made over a two minute period with the per-minute count derived from the average of the two minutes. Following the baseline measurement, the prototype formulation was administered over a six minute period using a commercial aqueous nebulizer (Pari Respiratory Equipment, Stamberg, Germany). Formulation 1 consisted of an isotonic saline solution. Formulation 2 consisted of a combination of phospholipids suspended in an isotonic saline vehicle. Following administration, exhaled particle counts were assessed 5 minutes, 30 minutes, one hour, two hours, and three hours after the single administration.

Figure 10A:
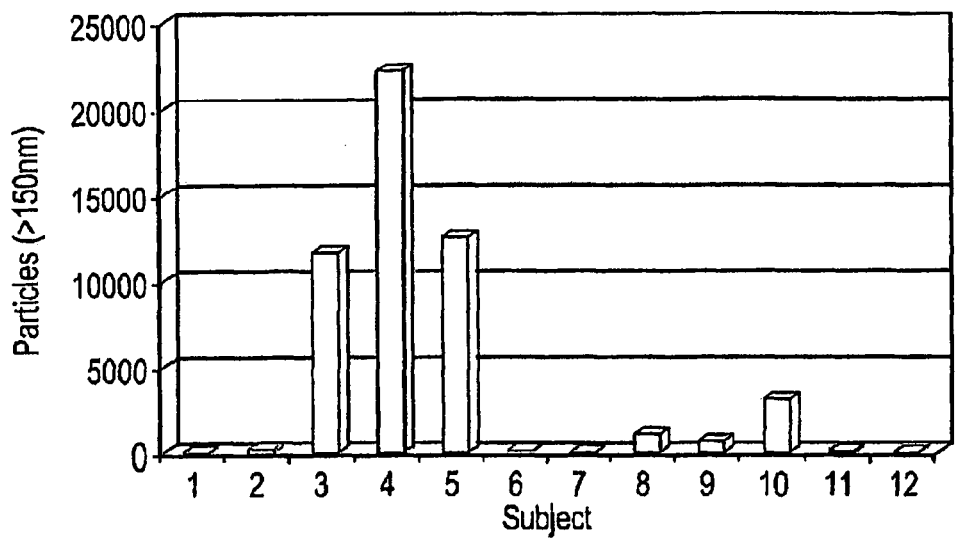
FIG. 10A is a chart of baseline particle count (greater than 150 nm) expired by individuals (n=11) while inhaling particle free air.
Figure 10B:
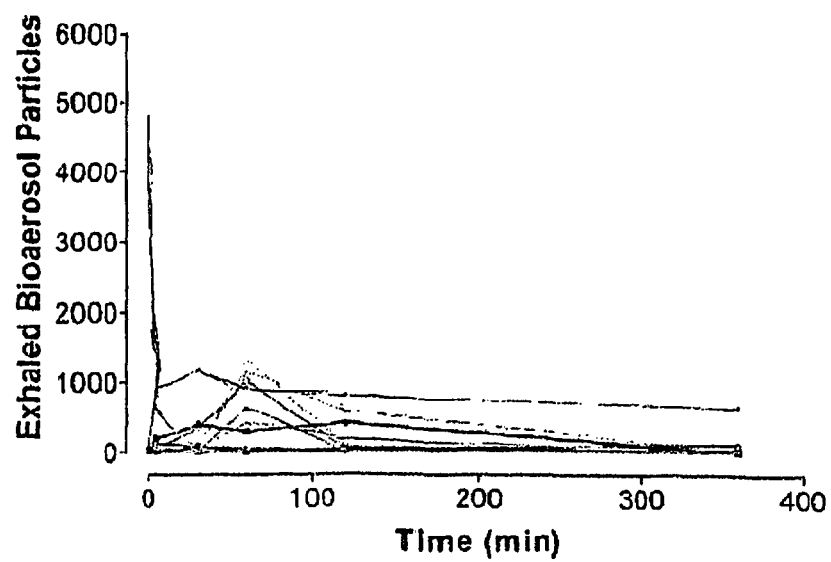
FIG. 10B is a graph of particle count (greater than 150 nm) expired by individuals (n=11) after saline (approximately 1 g) had been administered to the lungs in the form of an aerosol over time (minutes).

As shown in FIG. 10A, substantial inter-subject variability was found in baseline particle counts. The data shown are measurements made prior to administration of one of the test aerosols. This baseline expired particle result points to the existence of "super producers" of exhaled aerosols. In this study "super-producers" were defined as subjects exhaling more than 1,000 particles/liter at baseline measurement. FIG. 10B shows the individual particle counts for subjects receiving Formulation 1. The data indicate that a simple formulation of exogenously applied aerosol can suppress exhaled particle counts.

Figure 11A:
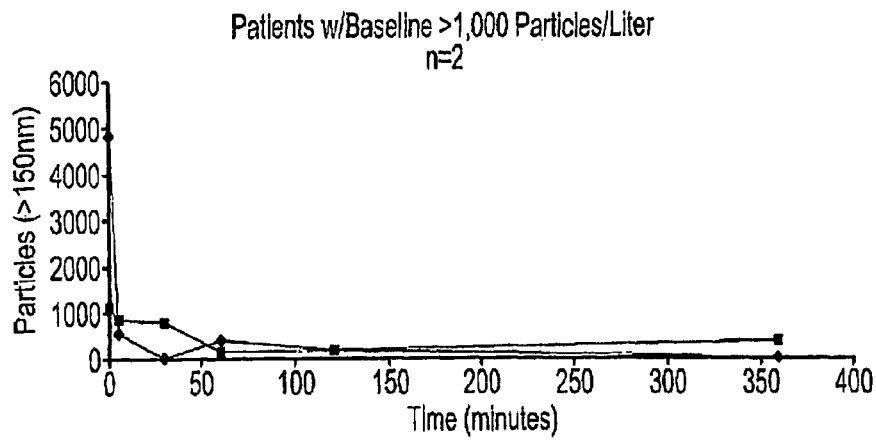
FIG. 11A is a graph of particle count (greater than 150 mm) exhaled by individuals (n=2) who, prior to treatment have a baseline exhalation of greater than 1000 particles/liter (while inhaling particle free air), after isotonic saline solution (approximately 1 g solution) had been administered to the lungs in the form of an aerosol over time (minutes)

FIG. 11A shows the effect of prototype formulation 1 on the two "super-producers" found at baseline in this group. These data indicate that the prototype formulation may exert a more pronounced effect on super-producers.

Figure 11B:
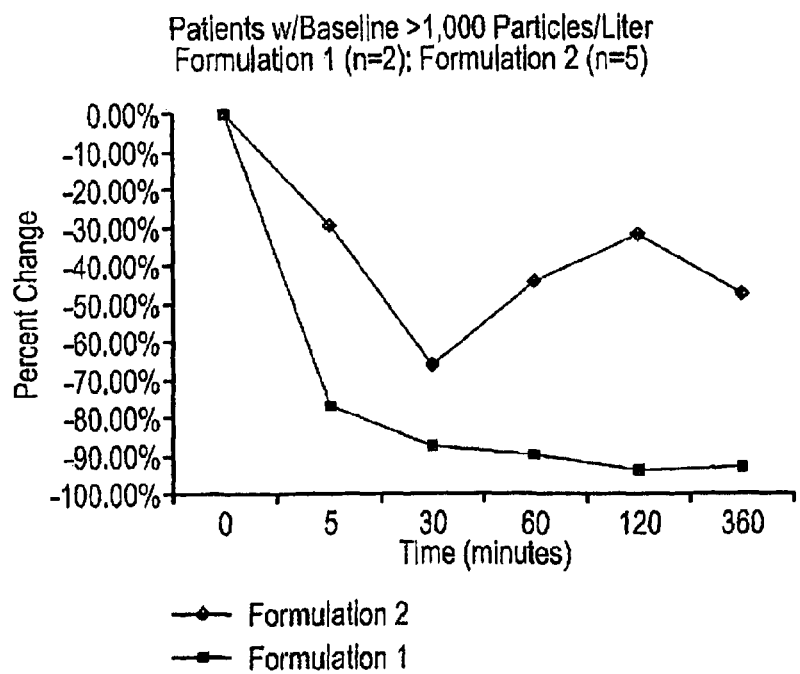
FIG. 11B is a graph of particle count (greater than 150 nm) exhaled by individuals (n=2) who, prior to treatment have a baseline exhalation of greater than 1000 particles/liter (while inhaling particle free air), after isotonic saline solution containing phospholipids (approximately 1 g solution) had been administered to the lungs in the form of an aerosol over time (minutes).

Similar results were found on delivery of formulation 2. FIG. 11B summarizes the percent change (versus baseline) of the cumulative exhaled particle counts for the "super-producers" identified in the two treatment groups. Results from this study demonstrate that exhaled particles can be accurately measured using a laser-detection system, that these particles are predominantly less than 1 micron in diameter, and that the number of these particles varies substantially from subject to subject. "Super-producing" subjects respond most markedly to delivery of an aerosol that modifies the physical properties of the surface of the lining fluid of the lungs. Such super-producers might bear significant responsibility for pathogen shedding and transmission in a population of infected patients. These data also demonstrate that suppressing aerosol exhalation is practical with relatively simple and safe exogenously administered aerosol formulations.

Example 3

Large Animal Study

Seven (7) Holstein bull calves were anesthetized, intubated, and screened for baseline particle exhalation by optical laser counting. Animals were subsequently untreated (sham) or treated with a nebulized aerosol of saline at one of three doses (1.8 minutes, 6.0 minutes or 12.0 minutes). During the sham dosage, the animals were handled in the same manner as they were when the dosages of the isotonic saline solution were administered. One animal was dosed per day and nebulizer doses were randomized throughout the exposure period (see Table 3 for dosing schedule). Each animal was slated to receive all doses during the duration of the study. Following the administration of each dose, exhaled particle counts were monitored at discrete timepoints (0, 15, 30, 45, 60, 90, 120) through 180 minutes.

The exposure matrix for the animals included in the study is found in Table 3. The dosing occurred over a 57 day period, with at least a 7 day interval between dosages. Each animal (n=7) received each dose at least once during the duration of dosing, with the exception of the omission of one 6.0 minute dose (see animal no. 1736) and one 12.0 minute dose (see animal no. 1735). These two were excluded due to unexpected problems with the ventilator and/or anesthesia equipment.

TABLE 3

Dosing Regime for Large Animals Dosage

| Animal No. | Sham | 1.8 min. | 6.0 min. | 12.0 min. |
| --- | --- | --- | --- | --- |
| 1731 | Day 17 | Day 3 | Day 10 | Day 25 |
| 1732 | Day 7 | Day 21 | Day 1 | Day 14 |
| 1735 | Day 18 | Day 11 | Day 4 | N/A |
| 1736 | Day 23 | Day 2 | N/A | Day 9 |
| 1738 | Day 8 | Day 15 | Day 36 | Day 25 |
| 1739 | Day 20 | Day 38 | Day 30 | Day 45 |
| 1741 | Day 50 | Day 35 | Day 57 | Day42 |

Results

Figure 12A:
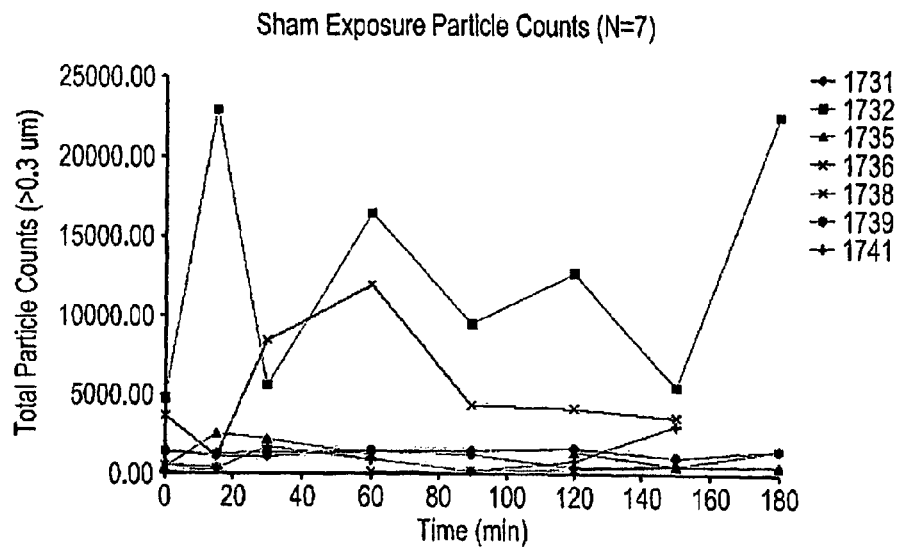
FIG. 12A is a graph of total particles exhaled (greater than 0.3 microns) over time (minutes) showing data obtained from sham treated animals.

FIG. 12A show the particle count over time for each animal after it received a sham dosage. Each timepoint typically represents the mean of at least three particle count determinations. The data in FIG. 12A shows that certain individual animals inherently produce more particles than others ("superspreaders"). Additionally, the data show that throughout the assessment period, quiescently breathing anesthetized animals maintain a relatively stable exhaled particle output (see e.g. Animal nos. 1731, 1735, 1738, 1739, and 1741).

Figure 12B:
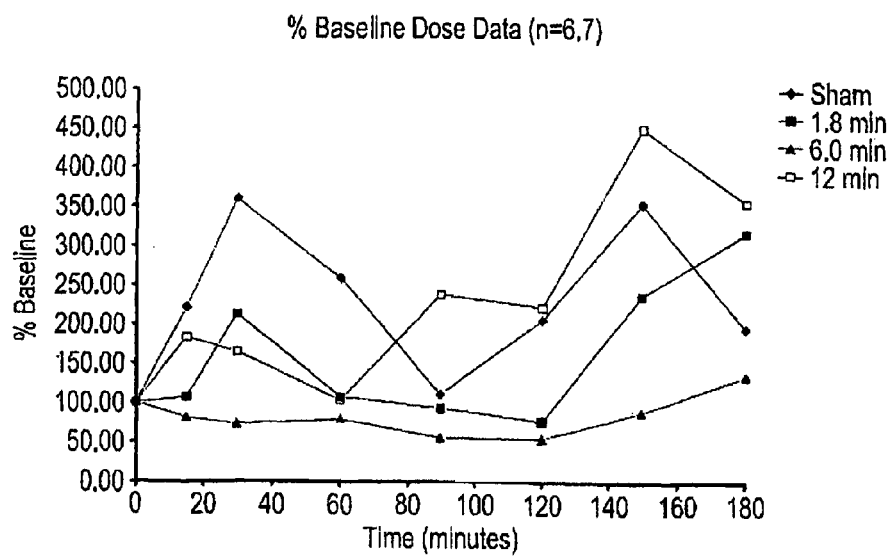
FIG. 12B is a graph of mean percent (%) baseline particle counts over time (minutes) showing data obtained from animals treated with nebulized saline for 1.8 minutes (-■-), 6.0 minutes (-▲-), 12.0 minutes (-□-), and sham (-♦-).

FIG. 12B represents the mean percent change in exhaled particle counts over time following each treatment. Each data point represents the mean of six to seven measurements from the treatment group. All animals had returned to baseline by 180 minutes post treatment. The data suggest that the 6.0 minute treatment period provides an adequate dose to prevent the exhalation of particles for at least 150 minutes post-treatment. The other treatments appear to be either too short or too long to provide an effective, lasting suppression of aerosol exhalation.

Example 4

Reduction of Exhaled Aerosol Particles in Human Study

In a study of 4 healthy adults, particle counts were measured using a device similar to that illustrated in FIG. 2 prior and subsequent to treatment with a formulation for reducing the number of exhaled particles. Treatment involved a six minute inhalation from a Pari LC+ jet nebulizer of a formulation containing 1.29% $CaCl_2$ by weight in 0.9% NaCl solution. Exhaled particles were measured prior to treatment and at timepoints 10 minutes, 1, 2, 4, and 6 hours after treatment completion. Total count rate of particles greater than 0.3 µm in diameter during a 3 minute test immediately following a 2 minute washout of ambient particles from the lungs was measured using a device similar to that illustrated in FIG. 2. The device contained a Climet CI-500B optical particle counter. This device accurately measured particles in the range of 300-2500 nm. A series of filters eliminated all background particle noise.

FIG. 13 shows the effect of the inhaled treatment on the count rate of particles greater than 0.3 µm particles produced. The mean count rate was seen to decrease from the baseline count rate prior to treatment for all timepoints up to 6 hours after treatment.

Example 5

Characterization of Exhaled Aerosol Particles in Human Study

In two separate studies, particle size distribution and number of particles produced during tidal breathing were measured in 580 adults and in 97 children using a measurement system similar to that illustrated in FIG. 2.

For both studies, the measurement system included a Fleisch pneumotachometer (model no. 1, Phipps and Bird, Richmond Va.) for measuring the patient flow rate during the test and an optical particle counter (Climet Model CI-500B, Climet Instruments Company, Redlands, Calif.) for measuring particle counts and size distribution over the range of 0.3-25 µm. Following a 2 minute washout period of breathing particle free air, the particle count rate was measured during a 3 minute test interval.

Similar to the smaller study from Example 2, large inter-subject variability was seen in the number of particles exhaled for both of the studies. In the adult study, 26% of the population was classified as "super producers", producing greater than 10,000 particles per minute and accounting for 94% of the particles measured in the study. The number of counts per minute ranged over nearly 5 orders of magnitude.

In the study of exhaled particle production in children, 12% of the population was classified as "super producers" by the same criteria and accounted for 86% of the total particles produced. Particle counts per minute again ranged over nearly 5 orders of magnitude.

Those skilled in the art will recognize, or be able to ascertain using no more than routine experimentation, many equivalents to the specific embodiments of the invention described herein. Such equivalents are intended to be encompassed by the following claims.

We claim:

1. A method for using a diagnostic device to measure the rate and size of particle exhalation in an individual, wherein the device comprises a mouthpiece, a two-way filter, a low resistance one-way valve, a particle counter, and a computer, wherein the mouthpiece comprises an outlet; wherein the outlet of the mouthpiece is connected to the filter and to the one-way valve, wherein the filter is exposed to the ambient environment at one end and connected to the mouthpiece at the other end, wherein the one-way valve is located inside a tube, wherein the tube is connected at an end distal to the outlet of the mouthpiece to the particle counter, and wherein the particle counter is connected to the computer, comprising (i) placing the mouthpiece in or over the individual's mouth or nose, (ii) inhaling air through the mouthpiece, wherein the air is pulled through the filter prior to inhalation, (iii) exhaling through the mouthpiece and into the one-way valve, (iv) measuring the number of particles and size of particles using the particle counter, and (v) providing the data from the particle counter to the computer.

2. The method of claim 1, wherein the device further comprises a gas flow meter connected to the filter and located between the filter and the ambient environment, a differential pressure transducer, wherein the differential pressure transducer is capable of measuring the pressure drop across the flow meter, and a signal conditioner, wherein the signal conditioner is connected to the differential pressure transducer and is capable of amplifying the signal and sending the to the computer.

3. The method of claim 2, wherein during step (ii) the air is pulled through the gas flow meter prior to being pulled through the filter.

4. The method of claim 1, further comprising prior to step (iii), providing data from the signal conditioner to the computer.

5. The method of claim 1, wherein steps (ii)-(v) are repeated multiple times.

6. The method of claim 5, further comprising (vi) calculating the mean particle size, the average particle distribution, and mean rate of particle production.

7. The method of claim 6, further comprising (vii) inhaling a formulation that when administered to the mucosal lining of a human or other animal alters the surface viscoelastic properties of the mucosal lining, surface tension of the mucosal lining, or bulk viscosity of the mucosal lining, and then repeating steps (i)-(vi).

8. The method of claim 7, wherein the formulation comprises a charged compound.

9. The method of claim 7, wherein the formulation is an aqueous, non-surfactant formulation.

10. The method of claim 7, wherein the formulation is in the form of an aerosol.

11. The method of claim 8, wherein the charged compound is selected from the group consisting of salts, ionic surfactants, charged amino acids, charged proteins or peptides, and combinations thereof.

12. The method of claim 10, wherein the formulation is saline.

13. The method of claim 1, wherein steps (i)-(v) occur prior to entering a clean room.

14. The method of claim 1, wherein prior to step (i), the user enters a cleanroom.

15. A method for using a diagnostic device to measure the rate and size of particle exhalation in an individual, wherein said diagnostic device comprises a disposable kit and a main housing, the disposable kit comprising a mouthpiece, a two-way filter, and a low resistance one-way valve, the main housing comprising a particle counter and a computer, and wherein the mouthpiece has an outlet connected to the filter and to the one-way valve, the filter is exposed to the ambient environment at one end and connected to the mouthpiece at the other end, wherein the filter is capable of removing particles having a size greater than or equal to 0.1 microns in diameter, and the disposable kit is connected to the main housing via two connecting tubes, said method comprising (i) placing the mouthpiece in or over the individual's mouth or nose, (ii) inhaling air through the mouthpiece, wherein the air is pulled through the filter prior to inhalation. (iii) exhaling through the mouthpiece and into the one-way valve, (iv) measuring the number of particles and size of particles using the particle counter, and (v) providing the data from the particle counter to the computer.

16. The method of claim 15, wherein the device further comprises a gas flow meter connected to the filter and located between the filter and the ambient environment and wherein during step (ii) the air is pulled through the gas flow meter prior to being pulled through the filter.

17. The method of claim 16, wherein the device further comprises a differential pressure transducer, capable of measuring the pressure drop across the flow meter, and a signal conditioner connected to the differential pressure transducer and capable of amplifying the signal and sending the signal to the computer and the method further comprises prior to step (iii), providing data from the signal conditioner to the computer.

18. The method of claim 15, wherein steps (ii)-(v) are repeated multiple times.

19. The method of claim 18, further comprising (vi) calculating the mean particle size, the average particle distribution, and mean rate of particle production.

20. The method of claim 19, further comprising (vii) inhaling a formulation that when administered to the mucosal lining of a human or other animal alters the surface viscoelastic properties of the mucosal lining, surface tension of the mucosal lining, or bulk viscosity of the mucosal lining, and then repeating steps (i)-(v).

21. A bi-directional flow meter system for measuring flow rates in a positive and a negative direction comprising:
   a) a main flow passage;
   b) a bypass line including a mass flow meter in fluid communication with the main flow passage through an upstream pressure tap and a downstream pressure tap, the mass flow meter being configured and adapted for measurement of flow rates within an effective range of flow rates; and
   c) a flow obstruction disposed within the main flow passage between the upstream and downstream pressure taps, wherein the flow obstruction is configured and adapted to provide mass flow rates to the mass flow meter that are within the effective range of the mass flow meter when the main flow passage is subject to respirable flow rates of inhalation and exhalation flows, wherein said respirable flow rates of inhalation and exhalation flows are between about +130 L/min and −70 L/min, wherein a positive flow rate corresponds to flow direction during exhalation, and wherein said flow obstruction is configured to maintain a laminar flow through itself for respirable flow rates.

22. A bi-directional flow meter system as recited in claim 21, wherein the flow obstruction is configured to provide mass flow rates to the mass flow meter that are within the effective range of the mass flow meter when the main flow passage is subject to flow rates between about +28 L/min and −28 L/min, wherein a positive flow rate corresponds to flow direction during exhalation.

23. A bi-directional flow meter system as recited in claim 21, wherein the upstream and downstream pressure taps are substantially equidistant from the flow obstruction.

24. A bi-directional flow meter system as recited in claim 21, wherein the flow obstruction includes a parallel array of cylindrical passages from an upstream face of the flow obstruction to a downstream face thereof.

25. A bi-directional flow meter system as recited in claim 24, wherein the flow obstruction is cylindrical and has a length from the upstream face to the downstream face that is substantially equal to the diameter of the cylindrical flow obstruction.

* * * * *